(12) United States Patent
Sirianni et al.

(10) Patent No.: US 10,952,967 B2
(45) Date of Patent: Mar. 23, 2021

(54) DRUG DELIVERY COMPOSITION AND METHOD OF FABRICATION

(71) Applicant: DIGNITY HEALTH, Phoenix, AZ (US)

(72) Inventors: Rachael Sirianni, Sugar Land, TX (US); Kyle Householder, Houston, TX (US); Danielle Diperna, New Haven, CT (US)

(73) Assignee: Dignity Health, Phoenix, AZ (US)

( * ) Notice: Subject to any disclaimer, the term of this patent is extended or adjusted under 35 U.S.C. 154(b) by 0 days.

(21) Appl. No.: 16/608,034

(22) PCT Filed: May 9, 2018

(86) PCT No.: PCT/US2018/031905
§ 371 (c)(1),
(2) Date: Oct. 24, 2019

(87) PCT Pub. No.: WO2018/208993
PCT Pub. Date: Nov. 15, 2018

(65) Prior Publication Data
US 2020/0054562 A1    Feb. 20, 2020

Related U.S. Application Data

(60) Provisional application No. 62/503,383, filed on May 9, 2017.

(51) Int. Cl.
*A61K 9/16* (2006.01)
*A61P 35/00* (2006.01)
(Continued)

(52) U.S. Cl.
CPC .......... *A61K 9/1641* (2013.01); *A61K 31/506* (2013.01)

(58) Field of Classification Search
None
See application file for complete search history.

(56) References Cited

U.S. PATENT DOCUMENTS

2013/0122058 A1    5/2013  Chow et al.
2014/0213641 A1    7/2014  Borros Gomez et al.
(Continued)

FOREIGN PATENT DOCUMENTS

WO    03/055469 A1     7/2003
WO    2016/012906 A1   1/2016

OTHER PUBLICATIONS

Sareen et al.,"Improvement in solubility of poor water-soluble drugs by solid dispersion", Int J Pharm Investig. Jan.-Mar. 2012; 2(1): 12-17 (Year: 2012).*

(Continued)

*Primary Examiner* — Kyung S Chang
(74) *Attorney, Agent, or Firm* — Rodney J. Fuller; Booth Udall Fuller, PLC

(57) ABSTRACT

The methods of manufacture of a drug delivery composition. In some aspects, the methods include providing an organic phase, a biologically active ingredient, and an aqueous phase with a desirable pH (e.g., a pH at which the active ingredient has increased solubility in the aqueous phase compared to at neutral pH). After mixing of one or more of the aforementioned components, the resultant mixture is processed to provide the desired drug delivery composition.

17 Claims, 8 Drawing Sheets

(51) Int. Cl.
*A61K 47/69* (2017.01)
*A61K 9/51* (2006.01)
*A61K 31/506* (2006.01)

(56) References Cited

U.S. PATENT DOCUMENTS

| | | |
|---|---|---|
| 2014/0249158 A1 | 9/2014 | Figueiredo et al. |
| 2015/0231070 A1 | 8/2015 | Huang |
| 2017/0042828 A1 | 2/2017 | Figueiredo et al. |
| 2018/0092857 A1* | 4/2018 | Shailubhai .............. A61P 43/00 |

OTHER PUBLICATIONS

Berg et al., Biochemistry, 5th edition, New York, W H Freeman 2002 (Year: 2002).*

Householder et al., "pH driven precipitation of quisinostat onto PLA-PEG nanopparticles enables treatment of intracranial glioblastoma", Colloids and Surfaces B: Biointerfaces, 166:37-44 (2018).

Feczko, Tivadar, "Sustained Delivery of Interferons by Micro- and Nanosystems", Recent Patents on Materials Science, 2(1):32-42 (Jun. 1, 2009).

Bowen, P., "Particle Size Distribution Measurement from Millimeters to Nanometers and from Rods to Platelets", Journal of Dispersion Science and Technology, 23(5):631-662 (Jan. 1, 2002).

* cited by examiner

DRUG DELIVERY COMPOSITION AND METHOD OF FABRICATION

CROSS-REFERENCE TO RELATED APPLICATIONS

This application is the U.S. National Stage of International Application No. PCT/US2018/031905, filed on May 9, 2018, which claims the benefit of U.S. Provisional Patent Application No. 62/503,383, filed on May 9, 2017, the contents of each of which are incorporated herein by reference in their entireties.

TECHNICAL FIELD

The disclosure relates to drug delivery compositions and methods of fabrication, and more particularly to drug delivery compositions and methods employing nanoparticles.

BACKGROUND

One of the key challenges to treating diseases, such as neoplastic diseases, is exposing the targeted tissue to a sufficiently high drug concentration. Numerous novel drug delivery strategies have been developed with the rapid advances of nanotechnology. For example, a nano-sized drug delivery system can address some of the known disadvantages of drugs, such as low bioavailability, poor solubility, and high cytotoxic side effects. Those of skill in the art have been attracted to the use of polymeric nanoparticles to deliver therapeutics for myriad reasons, including controlling drug release, structural design for targeting, and a functional design for delivery. However, a significant disadvantage of using nanoparticles for drug delivery is the manufacturing process often leads to relatively low yields and poor loading efficiency.

Histone deacetylases (HDACs) are known to be key enzymes in cancer development and progression through their modulation of chromatin structure and the expression and post-translational modification of numerous proteins. Aggressive dedifferentiated tumors, like glioblastoma, frequently overexpress HDACs, while HDAC inhibition can lead to cell cycle arrest, promote cellular differentiation, and induce apoptosis. Although multiple HDAC inhibitors, such as quisinostat, are of interest in oncology due to their potent in vitro efficacy, their failure in the clinic as monotherapies against solid tumors has been attributed to poor delivery. For example, some investigators report that the use of conventional nanoparticle-manufacturing processes results in only 1-2% drug loading of some histone deacetylase inhibitors, such as quisinostat.

With that difficulty in mind, the inventors of the systems and methods of drug delivery described herein sought to create new processes for drug delivery systems, compositions, and methodologies. The inventors were motivated to improve HDACi such as quisinostat loading onto polymeric nanoparticles (NPs) such as poly(D, L-lactide)-b-methoxy poly(ethylene glycol) NPs.

SUMMARY

The invention herein is directed to therapeutic nanoparticles, the manufacture thereof, and use in treatment of a subject. In one exemplary embodiment, the method of manufacturing therapeutic nanoparticles, comprises: mixing an organic phase with an aqueous phase to form a mixture, wherein the organic phase comprises an organic solvent and a nanoparticle comprising an amphiphilic polymer; adding a water insoluble biologically active ingredient, the active ingredient comprising an ionizable group and having a partition coefficient of log P>0, wherein the active ingredient is at least partially ionized in the aqueous phase, e.g., the active ingredient can be a weak acid; and removing the organic solvent from the mixture. In a particular embodiment, the active ingredient is at least 70%, 80%, 90% or 99% ionized in the aqueous phase and the active ingredient and the nanoparticle electrostatically interact.

The invention also encompasses a method of fabricating therapeutic nanoparticles by preparing an aqueous phase; adjusting the pH of the aqueous phase; mixing an organic phase containing a nanoparticle comprising an amphiphilic polymer with the aqueous phase; adding a water-insoluble biologically active ingredient, the active ingredient comprising an ionizable group; and removing the organic solvent; wherein the active ingredient has a higher water solubility in the adjusted pH than in a neutral pH.

The active ingredient can be added at different stages of the method, for example, after the organic solvent is partially removed. In exemplary embodiment, the method comprises dissolving the active ingredient in a solvent, e.g., dimethyl sulfoxide (DMSO), acetonitrile, or acetone.

In a specific exemplary embodiment, the method includes the steps of: (i) forming an organic phase comprising a polymer, such as an amphiphilic, hydrophobic, and/or hydrophilic polymer and an organic solvent; (ii) adding an active ingredient to the organic phase; (iii) forming an aqueous phase comprising a hydrophilic solvent, wherein the aqueous phase further comprise surfactant and/or a stabilizing agent; (iv) mixing together the organic phase and a first portion of the aqueous phase to form an emulsification mixture; (v) emulsifying the emulsification mixture; (vi) adjusting a pH of a second portion of the aqueous phase to a desired pH that improves solubility of the active ingredient; and/or (vii) mixing together the emulsification mixture with the second portion of the aqueous phase. In some embodiments, the method also include evaporating at least a portion of the organic solvent from the emulsification mixture after the addition of the second portion of the aqueous phase. Moreover, in some aspects, the desired pH is a basic pH. For example, the basic pH comprises a pH with a range of pHs that is greater than physiologic pH (a pH of around 7.4). In some embodiments, the basic pH is within a range of about 8 to about 14. In other aspects, the basic pH is around 10. In other embodiments, the pH is an acidic pH in a range of pHs that is less than physiologic pH. For example the acidic pH is within a range of about 1 to about 7. In other embodiments, the desired pH can be any pH that increases the solubility of the active ingredient within the aqueous phase.

In a non-limiting embodiment, the nanoparticles are prepared by emulsification, for example by forming a pre-emulsion organic phase comprising the amphiphilic polymer and the organic solvent; optionally, adding the active ingredient to the pre-emulsion organic phase; combining the pre-emulsion organic phase with a pre-emulsion aqueous phase to form a pre-emulsion mixture; and emulsifying the pre-emulsion mixture to form an emulsion.

In certain embodiments, the organic solvent comprises a solvent that is water miscible or water immiscible. For example, in those embodiments where the organic solvent is generally water immiscible, the organic solvent comprise at least one of the following water-immiscible solvents: dichloromethane (methylene chloride), chloroform, carbon tetrachloride, dichloroethane, diethyl ether, ethyl acetate, and toluene. In other embodiments where the solvent comprises a water-miscible solvent, the solvent, for example, comprises at least one of the following solvents: acetaldehyde, acetic acid, acetone, acetonitrile, cyclohexane, ethanol dimethyl formamide, dioxane, heptane, hexane, methanol, formic acid, ethylamine, ethylene glycol, dimethyl sulfoxide, glycerol, pentane, propanol, pyridine, tetrahydrofuran, and water.

Emulsification can employ any conventional emulsification procedures to emulsify the aqueous and organic phases. For example, in some embodiments, the emulsification step can comprise methods such as sonication and mechanical shearing (e.g., vigorous movement, such as stirring or homogenization with blades).

In some embodiments, prior to the addition to the organic phase, the active ingredient can be at least partially dissolved in a carrier, such as dimethyl sulfoxide. Moreover, in some embodiments, the active ingredient comprises an ionizable composition. For example, the ionizable composition is a therapeutic, such as a histone deacetylase inhibitor (e.g., quisinostat). In some aspects, the histone deacetylase inhibitor is used to treat one or more forms of cancer. In other embodiments, the histone deacetylase inhibitor is used to treat any other disease associated with aberrant histone deacetylase activity.

In particular embodiments, the surfactant or stabilizer comprises at least one of sodium cholate, sodium dodecyl sulphate, poloxamer, one or more Tween® compounds (Croda International of East Yorkshire, United Kingdom), vitamin E tocopheryl polyethylene glycol succinate, and polyvinyl alcohol. Moreover, the polymer may be an amphiphilic polymer selected from the group consisting of poly (lactic acid)-poly(ethylene glycol), poly(lactic-co-glycolic acid)-poly(ethylene glycol), poly(lactic-co-glycolic acid)-d-α-tocopheryl polyethylene glycol succinate, poly(lactic-co-glycolic acid)-ethylene oxide fumarate, poly(glycolic acid)-poly(ethylene glycol), polycaprolactone-poly(ethylene glycol), or any salts thereof. As provided above, the polymer can also be a hydrophobic and/or hydrophilic polymer.

The nanoparticles can also be prepared by nanoprecipitation. The nanoparticles can also be prepared in the presence of the active ingredient.

The therapeutic nanoparticles herein preferably comprise a biologically active ingredient and a nanoparticle, wherein the nanoparticle is an amphiphilic polymeric nanoparticle and the active ingredient comprises an ionizable group and has a partition coefficient of log P>0. Non-limiting examples of suitable ionizable groups include: hydroxamic acid group, carboxyl group, hydroxyl group, sulfhydryl group, phenolic group, amino group, imidazole group, guanidinium group, sulphonamide group, and imide group. The therapeutic nanoparticle preferably comprises at least 4%, more preferably at least 6%, or even more preferably, at least 9% of the active ingredient (% w/w).

In certain non-limiting embodiments, the active ingredient is at least partially loaded onto the surface of the polymeric nanoparticle, e.g., at least 30%, 60%, or 90%. The amphiphilic polymer in certain embodiments comprises PLA-PEG and has a weight averaged molecular weight of 2,000 to 60,000 daltons.

In certain embodiments the active ingredient comprises a histone deacetylase inhibitor, e.g., vorinostat (SAHA), istodax, belinostat, apicidin, SBHA, scriptaid, sodium butyrate, trichostatin A, entinostat, panobinostat, mocetinostat, romidepsin, tubastatin A, givinostat, dacinostat, quisinostat, pracinostat, droxinostat, abexinostat, ricolinostat, tacedinaline, tubacin, resminostat, citarinostat, santacruzamate, nexturastat A, tasquinimod, parthenolide, and any pharmaceutically acceptable salts thereof.

The hydrodynamic diameter of the therapeutic nanoparticle is preferably between 20-300 nm, e.g., 50-200 nm. Furthermore, preferably the therapeutic nanoparticle has a zeta potential of between −35 and +10 mV, more preferably between −10 and +10 mV.

In a particular non-limiting embodiment, the therapeutic nanoparticle comprises a second biologically active ingredient, wherein the second active ingredient is encapsulated in the polymeric nanoparticle, e.g., entrapped in the polymeric nanoparticle.

The invention is also directed to the use of the therapeutic nanoparticles described herein, in the manufacture of a medicament for the treatment of a disorder and also to a method of treating a subject having a disorder, e.g., cancer.

DETAILED DESCRIPTION

Figure 1:
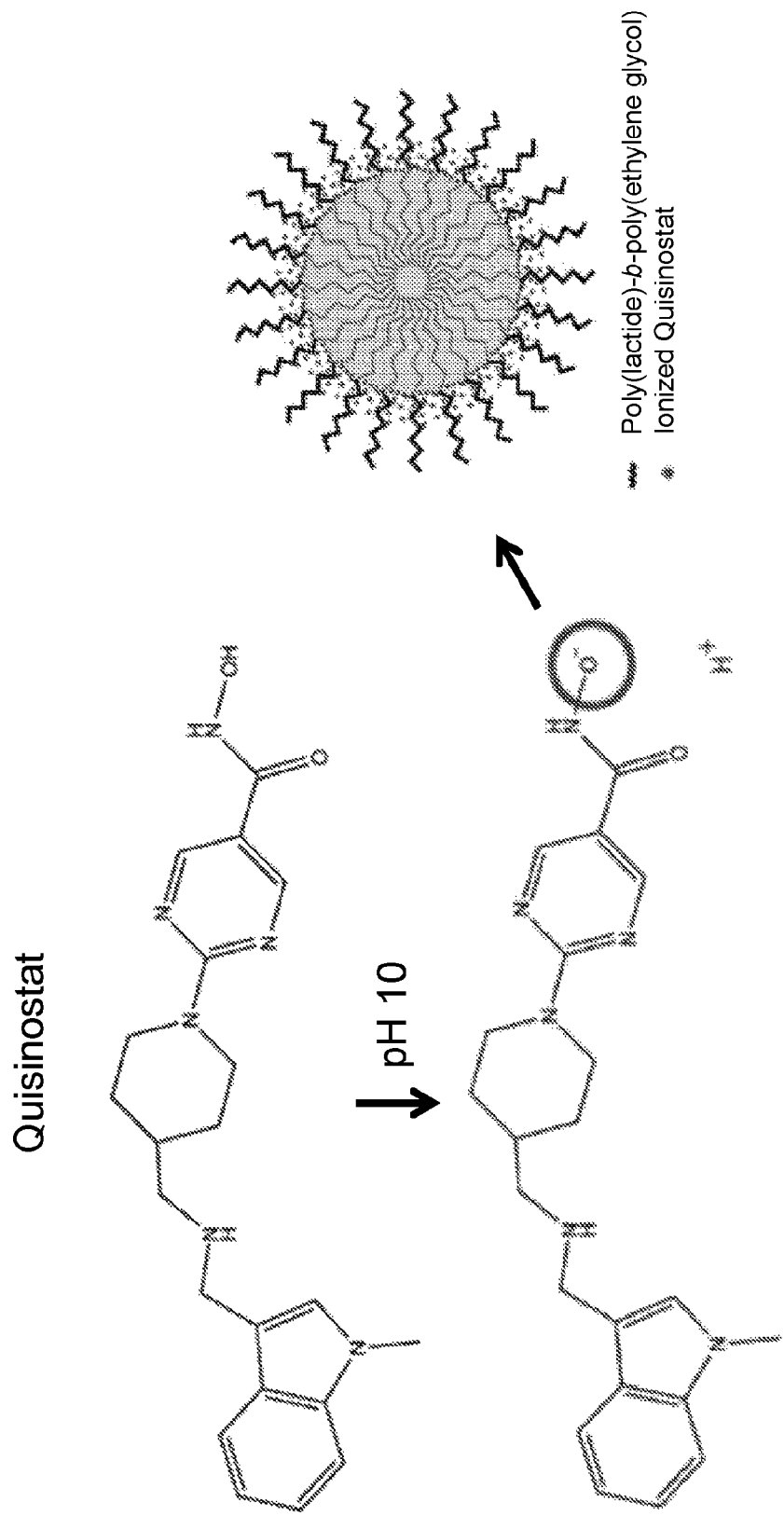
FIG. 1 depicts the novel pH driven approach for achieving high quisinostat loading of PLA-PEG NPs. Deprotonation of the hydroxamic acid group of quisinostat at pH 10 increases electrostatic interaction between quisinostat and the surface of the PLA-PEG NPs.

Additional objectives, advantages, and novel features will be set forth in the description which follows or will become apparent to those skilled in the art upon examination of the detailed description which follows.

As provided in greater detail herein, the disclosure provides drug delivery compositions, methods of fabrication, use of drug delivery compositions in the manufacture of a medicament, and methods of administration. In some embodiments, the disclosure comprises a methodology of the fabrication of a drug delivery composition. In other embodiments, the disclosure comprises a methodology of the administration of a drug delivery composition for the treatment of one or more diseases or disorders.

The drug delivery composition or method disclosed herein at least partially rely on and incorporate one or more aspects of nanotechnology. In some embodiments, the drug delivery composition comprises a therapeutic nanoparticle. As used herein, the term "therapeutic nanoparticle" refers to therapeutics in nanoparticle systems having the potential to increase drug-loading capabilities, improve site-specific delivery, controlled release, or a combination thereof. Therapeutics in nanoparticle systems have been shown to improve drugs pharmacokinetics through prolonged circulation, passive accumulation in the target site, and prolonged drug release.

Biologically Active Ingredient

In some aspects, the therapeutic nanoparticle comprises a biologically active ingredient. As used herein, "a biologically active ingredient" includes a compound, a molecule, a composition, a structure, and an element, etc. In some embodiments, the biologically active ingredient includes a therapeutics capable of treating a disease or a disorder. Non-limiting examples of the disease or disorder include neoplastic diseases such as cancer, neurodegenerative diseases, multiple sclerosis (MS), diabetes, HIV, tuberculosis, psoriasis, arthritis, asthma, ischemic related diseases, eye diseases, steroids deficiencies, and addictions, etc.

Non-limiting examples of cancer include solid tumors and blood-borne cancers, etc. Non-limiting examples of solid tumor include fibrosarcoma, myxosarcoma, liposarcoma, chondrosarcoma, osteogenic sarcoma, chordoma, angiosarcoma, endotheliosarcoma, lymphangiosarcoma, leiomyo sarcoma, synovioma, mesothelioma, Ewing's tumor, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, and lymphangioendotheliosarcoma, etc. Non-limiting examples of blood-borne cancer include acute lymphoblastic leukemia (ALL), acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia (CML), chronic lymphocytic leukemia (CLL), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera, etc.

Non-limiting examples of the neurodegenerative disease include Huntington's disease (HD), Alzheimer's disease (AD), Parkinson's disease (PD), motor neuron disease, Schizophrenia, and amyotrophic lateral sclerosis (ALS), etc. Non-limiting examples of ischemic related diseases include glaucoma, retinopathy, and macular degeneration, etc. Non-limiting examples of addiction include alcohol addiction and nicotine addiction, etc.

In some embodiments, the biologically active ingredient includes, for example, a histone deacetylase inhibitor (HDACi). As is known in the art, HDACs are overexpressed in many types of cancers. Overexpression of HDACs induces histone deacetylation and in turn, chromatin compaction. Chromatin compaction can further result in transcriptional suppression of key genes involved in the prevention or suppression of tumorigenesis. As such, inhibition of HDAC activities via the administration of HDACi(s) can reduce inhibition of tumor-suppressing genes, leading to improved tumor suppression. Furthermore, aberrant HDAC activity or expression has also been shown to cause non-cancerous diseases.

Non-limiting examples of HDACi include quisinostat, vorinostat (SAHA), istodax, belinostat, apicidin, SBHA, scriptaid, sodium butyrate, trichostatin A, entinostat, panobinostat, mocetinostat, romidepsin, tubastatin A, givinostat, dacinostat, pracinostat, droxinostat, abexinostat, ricolinostat, tacedinaline, tubacin, resminostat, citarinostat, santacruzamate, nexturastat A, tasquinimod, parthenolide, any pharmaceutically acceptable salts of any of the foregoing, and any derivatives of any of the foregoing, etc. In some aspects, the biologically active ingredient includes quisinostat, a derivative or salt thereof.

As used herein, the term "derivative" refers to a compound that is synthesized from a parent compound by replacement of one atom with another atom or group of atoms. Non-limiting examples of derivative include a salt, a pharmaceutically acceptable salt, and chemical modifications with a group including but not limited to esters, fluorine, methoxy, ethyl, butyl, propyl, hexyl, or other organic moieties.

In certain non-limiting embodiments, a therapeutic nanoparticle comprising an HDACi is used for the treatment of cancer, e.g., hematological cancer or a solid tumor. In other embodiments, a therapeutic nanoparticle comprising an HDACi is used for the treatment of a non-cancerous disease. In some non-limiting embodiments, a therapeutic nanoparticle comprising quisinostat is used for the treatment of hematological cancer, a solid tumor, or both. In yet further non-limiting embodiments, a therapeutic nanoparticle comprising quisinostat is used for the treatment of glioma, for example, glioblastoma multiforme ("GBM").

In some aspects, the active ingredient is water insoluble. As used herein, the term "water insoluble" refers to an active ingredient having a partition coefficient (log P) of at least 0. In some embodiments, the active ingredient, for example, HDACi, has a log P selected from the group consisting of at least 0, at least 0.3, at least 0.7, at least 1, at least 1.3, at least 1.7, at least 2, at least 2.5, and at least 3. In other embodiments, log P is between 0 and 3, or any number range in between, e.g., 0-2.6, 0.1-2.6, 0.1-2.2, 0.2-2.2, 0.2-1.8, 0.4-1.8 or 0.4-1.4. In yet other embodiments, the active ingredient, for example, HDACi, has a log P selected from the group consisting of between 0 and 2, or any number range in between, e.g., 0-1.8, 0.2-1.8, 0.2-1.6, 0.4-1.4, 0.4-1.2, 0.4-1, or 0.5-2.

In some aspects, the water solubility of the active ingredient is, e.g., less than 1 mg/ml, less than 0.5 mg/ml, less than 0.2 mg/ml, less than 0.15 mg/ml or less than 0.1 mg/ml. In some embodiments, the water solubility of the active ingredient is between 0.01 and 1 mg/ml, or any number range in between, e.g., 0.02-1 mg/ml, 0.02-0.8 mg/ml, 0.04-0.8 mg/ml, 0.04-0.6 mg/ml, 0.05-0.6 mg/ml, 0.05-1 mg/ml or 0.05-0.5 mg/ml. As used herein, the term "water solubility" refers to the solubilities of the active ingredient in water, at a pressure of 1 atm and at room temperature (approx. 293.15 K).

In some embodiments, the active ingredient is an ionizable compound including an ionizable group. As used herein, "ionizable" refers to capable of dissociating atoms or molecules into electrically charged species; "an ionizable compound" refers to any molecule, composition, structure, element, etc., that, under certain conditions, having one or more atoms or molecules dissociated therefrom and form electrically charged compounds, radicals, or both; and "ionizable group" refers to an uncharged group act as proton-donor or proton acceptor influencing the capacity for a molecule to act as an acid or base. Non-limiting examples of the ionizable group include a hydroxamic acid group, a hydroxyl group, a carboxyl group, a sulfhydryl group, a phenolic group, an amino group, an imidazole group, a guanidinium group, a sulphonamide group, and an imide group, or a combination thereof. In some aspects, the active ingredient (e.g., an HDACi) has a carboxyl group, a hydroxamic acid group, or both. For example, Quisinostat comprises a hydroxamic acid group.

In some embodiments, the active ingredient is 100% ionized in the aqueous phase. In other embodiments, the active ingredient is partially ionized. As used herein, "partially ionized" refers to less than 100% ionized in the aqueous phase. For example, the active ingredient is between 10% and 99% ionized, or any percent range in between, e.g., 10-90%, 20-90%, 20-80%, 40-80% or 50-90%. In some aspects, the active ingredient is at least 20%, at least 50%, at least 70% or at least 90% ionized in the aqueous phase.

In other embodiments, the ionization of the active ingredient is increased in the aqueous solution compared to neutral pH, by between 10% to 90%, or any percent range in between, e.g., increased by about 20% (e.g., 10-30%), by about 30% (e.g., 20-40%), by about 40% (e.g., 30-50%), by about 50% (e.g., 40-60%), by about 60% (e.g., 50-70%) or by about 70% (e.g., 60-80%).

Under some circumstances, the ionization state of a specific ionizable group of the biologically active ingredient is critical for water solubility of the active ingredient. In some embodiments, the specific ionizable group is between 50% and 100% ionized in the aqueous phase, or any percent range in between, e.g., 50-90%, 60-90%, 60-80% or 70-80%. In other embodiments, the specific ionizable group is at least 50%, at least 60% or at least 70% ionized in the aqueous phase. In yet other embodiments, the ionization of the active ingredient is increased in the aqueous solution compared to neutral pH, by between 10% to 90%, or any percent range in between, e.g., increased by about 20% (e.g., 10-30%), by about 30% (e.g., 20-40%), by about 40% (e.g., 30-50%), by about 50% (e.g., 40-60%), by about 60% (e.g., 50-70%) or by about 70% (e.g., 60-80%).

In further non-limiting embodiments, the hydroxamic acid group of quisinostat is between 50% and 100% ionized in the aqueous phase, or any percent range in between, e.g., 50-90%, 60-90%, 60-80% or 70-80%. In other embodiments, the hydroxamic acid group of quisinostat is at least 50%, at least 60% or at least 70% ionized in the aqueous phase. In further embodiments, the ionization of the hydroxamic acid group is increased in the aqueous solution compared to neutral pH, by between 10% to 90%, or any percent range in between, e.g., increased by about 15% (e.g., 5-25%), by about 25% (e.g., 15-35%), by about 35% (e.g., 25-45%), by about 50% (e.g., 40-60%), by about 60% (e.g., 50-70%) or by about 70% (e.g., 60-80%).

Some embodiments of the disclosure comprise adding the active ingredient to a solvent. Selection of the solvent is, at least in part, based on the chemical structure of the active ingredient. As used herein, the term "solvent" refers to any suitable liquid, compound, or molecule that functions to solubilize the active ingredient in a state. In some aspects, the active ingredient is partially solubilized in the solvent. In other aspects, the active ingredient is completely solubilized in the solvent.

Non-limiting examples of the solvent include dimethyl sulfoxide (DMSO), acetonitrile, acetone, and a combination thereof. In some embodiments, a hydrophobic active ingredient is added to DMSO, acetonitrile or acetone. In other embodiments, an HDACi is added to DMSO or acetone. In yet other embodiments, quisinostat is added to DMSO.

In some embodiments, the therapeutic nanoparticle comprises a single active ingredient. In other aspects, the single active ingredient is configured as a hybrid molecule, such that one active ingredient possesses different functionalities. In yet other aspects, the therapeutic nanoparticle comprises two or more active ingredients. In some embodiments, the second active ingredient is encapsulated in the therapeutic nanoparticle, for example, the polymeric nanoparticle. In other embodiments, the second active ingredient is entrapped in the polymeric nanoparticle. In yet other embodiments, the second active ingredient is dissolved in the polymeric nanoparticle. In further embodiments, the second active ingredient is associated with or non-covalently interacting with the polymeric nanoparticle. In yet further embodiments, the second active ingredient is loaded into, loaded onto or precipitated onto the polymeric nanoparticle.

Nanoparticle (NP) Preparation

As described herein, at least a portion of the drug delivery composition comprises one or more nanoparticles. Techniques used to prepare nanoparticles include but are not limited to the spontaneous formation of nanoparticles (e.g., salting out or nanoprecipitation), emulsion diffusion, emulsion evaporation, precipitation polymerization, emulsion and microemulsion polymerization, and interfacial polymerization.

Nanoparticles for drug delivery include numerous architectural designs in terms of size, shape, and materials. These include dendrimers, micelles, nanospheres, nanocapsules, fullerenes and nanotubes, and liposomes, etc. It is known in the art that the characteristics of each particle differ in terms of drug loading capacity, particle and drug stability, drug release rates, and targeted delivery ability. In certain embodiments, the nanoparticles are fabricated using conventional components, such as a solid particle (e.g., an Au- or Fe-based core nanoparticle), a liposome (or other lipid-derived materials), a micelle, a reverse micelle, or a microsphere, etc.

In some aspects, the nanoparticles are fabricated using one or more polymer-based nanoparticles (polymeric nanoparticles), selected in accordance with the anticipated use and the type and structure of the active ingredient used therewith.

In some embodiments, the polymeric nanoparticles comprise a hydrophobic polymer. In other embodiments, the polymeric nanoparticles comprise a hydrophilic polymer. In yet other embodiments, the polymeric nanoparticles comprise an amphiphilic polymer. In some aspects, the polymeric nanoparticles comprise substantially all hydrophobic polymers. In other aspects, the polymeric nanoparticles comprise substantially all hydrophilic polymers. In yet other embodiments, the polymeric nanoparticles comprise a combination, e.g., a hydrophilic polymer and an amphiphilic polymer.

Non-limiting examples of the types of the amphiphilic polymer include amphiphilic copolymer (e.g., a copolymer of a hydrophilic block coupled with a hydrophobic block), amphiphilic graft copolymer, amphiphilic block copolymer and amphiphilic random copolymer, etc.

Non-limiting examples of the amphiphilic polymer include poly(lactic acid)-poly(ethylene glycol) (PLA-PEG), poly(lactic-co-glycolic acid)-poly(ethylene glycol) (PLGA-PEG), poly(lactic-co-glycolic acid)-d-α-tocopheryl polyethylene glycol succinate, poly(lactic-co-glycolic acid)-ethylene oxide fumarate, poly(glycolic acid)-poly(ethylene glycol), polycaprolactone-poly(ethylene glycol), any salts of the foregoing, and any derivatives of the foregoing, etc.

In some non-limiting embodiments, the amphiphilic polymer comprises PLA-PEG, PLGA-PEG or any derivatives or salts thereof. In some embodiments, the HDACi-loaded nanoparticles comprise PLA-PEG, PLGA-PEG, or both. In other embodiments, the quisinostat-loaded nanoparticles comprise PLA-PEG or any derivatives or salts thereof.

In some aspects, the PLA-PEG has a weight averaged molecular weight of between 2,000 and 60,000 daltons, or any number range in between, e.g., 3,000-60,000, 3,000-50,000, 5,000-50,000, 5,000-40,000, 8,000-40,000, 8,000-30,000, or 10,000-20,000 daltons.

In some aspects, the PLA-PEG block co-polymer comprises polymer chain having an about 16 k Da (e.g., 15 k to 17 k Da) PLA segment attached to an about 5 k Da (e.g., 4 k to 6 k Da) PEG segment. In other aspects, the PLA-PEG block co-polymer comprises polymer chain having an about 20 k Da (e.g., 19 k to 21 k Da) PLA segment attached to an about 5 k Da (e.g., 4 k to 6 k Da) PEG segment.

In other embodiments, the amphiphilic polymer includes PLA and PEG.

As used herein, "PLA" refers to a polymer derived from the condensation of lactic acid or by the ring opening polymerization of lactide. In some aspects, the weight averaged molecular weight of PLA is between 5,000 and 35,000 daltons, or any number range in between, e.g., 5,000-30,000, 8,000-30,000, 8,000-25,000, 11,000-25,000, 11,000-21,000, 14,000-21,000, 14,000-19,000, 15,000-17,000, or 17,000-19,000 daltons. In other aspects, the PLA has a weight averaged molecular weight of about 16,000 daltons (e.g., 15,000-17,000 daltons) or about 20,000 daltons (e.g., between 19,000-21,000 daltons).

In some embodiments, the weight averaged molecular weight of PEG is between 1,000 and 10,000 daltons, or any number range in between, e.g., 1,000-9,000 daltons, 2,000-9,000 daltons, 2,000-8,000 daltons, 3,000-8,000 daltons, 3,000-7,000 daltons, 4,000-7,000 daltons, or 4,000-6,000 daltons. In other embodiments, the weight averaged molecular weight of PEG is about 5,000 daltons, for example, between 4,500 and 5,500 daltons or between 4,000 and 6,000 daltons.

In some aspects, the ratio of PLA and PEG (PLA:PEG) is between 50:5 and 10:5, or any number range in between, e.g., about 40:5, about 35:5, about 30:5, about 20:5 or about 16:5.

In yet other embodiments, the polymeric nanoparticles comprise two or more amphiphilic polymers.

Organic Phase

The method of fabricating the therapeutic nanoparticles comprises mixing an organic phase with an aqueous phase. In some aspects, the organic phase is formed by combining a polymer with an organic solvent. In other aspects, the organic phase is formed by combining a nanoparticle, for example, a solid/non polymer nanoparticle (e.g., iron oxide core), with an organic solvent.

In some embodiments, the polymer is mixed in the organic solvent. In other embodiments, the polymer is dissolved in the organic solvent. In particular non-limiting embodiments, an amphiphilic polymer, such as poly(lactic acid)-poly(ethylene glycol) (i.e., PLA-PEG and/or PLA-b-PEG) is dissolved in an organic solvent, such as DCM. In further non-limiting aspects, the organic phase comprising the amphiphilic polymer is an emulsion.

In some non-limiting embodiments, the nanoparticles are prepared using emulsification, and the organic solvent includes a water-immiscible solvent. Non-limiting examples of the water-immiscible solvent include dichloromethane (DCM, methylene chloride), chloroform, carbon tetrachloride, dichloroethane, diethyl ether, ethyl acetate, and toluene, etc. In some aspects, for example, the organic phase comprises PLA-PEG nanoparticles and DCM. In other non-limiting embodiments, the nanoparticles are prepared using emulsification, and the organic solvent includes water-miscible mixed with water-immiscible solvents. In yet other non-limiting embodiments, the nanoparticles are prepared using nanoprecipitation, and the organic solvent includes a water-miscible solvent. Non-limiting examples of the water-miscible solvent include acetaldehyde, acetic acid, acetone, acetonitrile, cyclohexane, ethanol, dimethylformamide, dioxane, heptane, hexane, methanol, formic acid, ethylamine, dimethyl sulfoxide, pentane, propanol, pyridine, and tetrahydrofuran, etc.

In some aspects, a physical force (e.g., mixing, vortexing, or shaking) is applied to the polymer-organic solvent mixture to dissolve the polymer in the organic solvent. In other aspects, the amphiphilic polymer will go into solution without the addition of any significant or material physical force.

Aqueous Phase

In certain non-limiting embodiments, the aqueous phase comprises one or more hydrophilic solvents (e.g., water).

In some embodiments, the aqueous phase comprises a surfactant. As used herein, the term "surfactant" refers to any substance that tends to reduce the surface tension between two different molecules. For example, between two liquids or between a liquid and a solid (e.g., the aqueous phase and the active ingredient). Non-limiting examples of the surfactant include sodium cholate, sodium dodecyl sulphate, poloxamer, one or more Tween® compounds, vitamin E tocopheryl polyethylene glycol succinate, and polyvinyl alcohol, etc. Some aspects of the disclosure include dissolving the surfactant in the aqueous phase using a physical force (e.g., mixing, vortexing, or shaking). Other aspects of the disclosure require no significant or material physical force for dissolving the surfactant in the aqueous phase. In some aspects, the surfactant acts as an emulsifier to provide for a mixing of the organic phase and the aqueous phase.

In other embodiments, the aqueous phase comprises a stabilizer. As used herein, the term "stabilizer" refers to any substance capable of inhibiting the separation of the organic phase and the aqueous phase. Non-limiting examples of the stabilizer include sodium cholate, sodium dodecyl sulphate, poloxamer, one or more Tween® compounds, vitamin E tocopheryl polyethylene glycol succinate, and polyvinyl alcohol, etc. Some aspects of the disclosure include dissolving the stabilizer in the aqueous phase using a physical force (e.g., mixing, vortexing, or shaking). Other aspects of the disclosure require no significant or material physical force for dissolving the stabilizer in the aqueous phase. In some aspects, the stabilizer acts as an emulsifier to provide for a mixing of the organic phase and the aqueous phase.

In yet other embodiments, the aqueous phase comprises a surfactant and a stabilizer.

In certain non-limiting embodiments, the aqueous phase comprises sodium cholate, TPGS or PVA. In other non-limiting embodiments, the aqueous phase comprises sodium cholate.

"Critical micelle concentration" (CMC) depends on temperature and sometimes pH, among other parameters. For sodium cholate, the "critical micelle concentration" values are roughly 8, 8, 9, 9, and 11 mmol dm$^{-3}$ at 293.2, 298.2, 303.2, 308.2, and 313.2 K. In certain non-limiting embodiments, the weight percent (% w/w) of sodium cholate is between 0-1%, or any number range in between, e.g., 0.01-1%, 0.01-0.9%, 0.02-0.9%, 0.02-0.8%, 0.05-0.8%, 0.05-0.6% or 0.1-0.6%.

Some embodiments of the disclosure includes adjusting the pH of the aqueous phase to increase the water solubility of the active ingredient. In some aspects, pH of the aqueous phase is reduced to improve the water solubility of the active ingredient, for example, by adding an acidic solution such as hydrochloric acid. In other aspects, pH of the aqueous phase is increased to improve the water solubility of the active ingredient, for example, by adding a basic solution such as sodium hydroxide. In further aspects, a buffer with appropriate pKa is added to control the pH of the aqueous solution.

Drug Loading

In some embodiments, the active ingredient is added to the mixture of the organic phase and the aqueous phase after NP formation. In other embodiments, the active ingredient is added to the mixture during the removal step (i.e., when the organic solvent is partially removed). In yet other embodiments, the active ingredient is added to the organic solvent comprising the polymer.

As used herein, "encapsulation efficiency" of the active ingredient is calculated using the following equation:

$$\text{encapsulation efficiency}(\%) = \frac{\text{mass of active ingredient in } NPs}{\text{mass of active ingredient used in the formulation}} \times 100$$

In some embodiments, the encapsulation efficiency of the active ingredient is between 50-100%, or any percent range in between, e.g., 55-100%, 55-90%, 60-95%, 60-90%, 65-95% or 65-90%. In other embodiments, the encapsulation efficiency of the active ingredient is at least 50%, at least 55%, at least 60%, at least 70% or at least 80%. In other non-limiting embodiments, the encapsulation efficiency of HDACi is between 50-95%, between 55-85% or 60-80%. In other non-limiting embodiments, the encapsulation efficiency of quisinostat is between 50-100%, between 55-90%, between 60-80% or at least 60%.

The Therapeutic Nanoparticles

As used herein, "content of the active ingredient" in the therapeutic nanoparticles (%, w/w) is calculated using the following equation:

$$\text{active ingredient content}(\% \ w/w) = \frac{\text{mass of active ingredient in } NPs}{\text{mass of } NPs \text{ recovered}} \times 100$$

In some embodiments, the content of the active ingredient in the therapeutic nanoparticles is, for example, at least 2%, at least 5%, at least 10%, at least 15%, or at least 20%. In other embodiments, the content of the active ingredient in the therapeutic nanoparticles is between 2.5-20%, or any percent range in between, e.g., 2.5-17%, 2.5-14%, 2.5-11%, 4-19%, 4-16%, 4-13%, 6-18%, 6-15%, 6-12%, 8-17%, 8-14% or 8-11%.

In other non-limiting embodiments, content of HDACi in the polymeric nanoparticles is between 5-15%, or any percent range in between, e.g., 5-13%, 5-11%, 6-14%, 6-12%, 7-15%, 7-12% or 8-12%.

In yet other embodiments, the content of quisinostat in the therapeutic nanoparticles is, for example, about 3% (e.g., 2-4%), about 5% (e.g., between 3% and 7.5%), about 10% (e.g., between 7% and 13%) or about 15% (e.g., between 10% and 20%). In this context, "about" refers to ±30%.

In some non-limiting aspects, the content of quisinostat in the polymeric nanoparticles is between 2-20%, or any percent range in between, e.g., 3-18%, 3-16%, 4-15%, 5-15%, 6-14%, 6-13%, 7-12% or 7-11%.

In some embodiments, the hydrodynamic diameter of the therapeutic nanoparticle is 20 to 300 nm, or any number range in between, e.g., 20 to 250 nm, 40 to 250 nm, 40 to 200 nm, 80 to 200 nm or 80 to 150 nm.

In other embodiments, the hydrodynamic diameter of HDACi-loaded therapeutic nanoparticle is about 50 nm (e.g., 20-80 nm), about 75 nm (e.g., 45-105 nm), about 100 nm (e.g., 70-130 nm), about 150 nm (e.g., 120-180 nm), about 200 nm (e.g., 170-230 nm) or about 250 nm (e.g., 220-280 nm).

In yet other non-limiting embodiments, the hydrodynamic diameter of quisinostat-loaded PLA-PEG therapeutic nanoparticle is between 50-200 nm, or any number range in between, e.g., 50-180 nm, 70-180 nm, 70-150 nm, 90-150 nm or 90-120 nm.

In some embodiments, the zeta potential of the therapeutic nanoparticles is −50 to +50 mV, or any number range in between, e.g., between −50 to +30 mV, between −35 to +20 mV, between −35 and +10 mV, between −20 and +15 mV, between −20 and +10 mV or between −10 and +10 mV.

In other non-limiting embodiments, the zeta potential of the HDACi-loaded polymeric nanoparticles is about −35 mV (e.g., between −50 and −20 mV), about −15 mV (e.g., between −25 and −5 mV), about −10 mV (e.g., between −20 and 0 mV) or about −0 mV (e.g., between −10 and +10 mV).

In some non-limiting aspects, the zeta potential of the quisinostat-loaded therapeutic nanoparticles is between −25 mV and 0 mV, between −20 mV and 0 mV, between −16 mV and 0 mV, or between −14 mV and 0 mV. In other non-limiting aspects, the zeta potential of the quisinostat-loaded polymeric nanoparticles is about −20 mV (e.g., between −30 and −10 mV), about −15 mV (e.g., between −25 and −5 mV) or about −10 mV (e.g., between −20 and 0 mV).

In some embodiments, the active ingredient is partially loaded onto the surface of the polymeric nanoparticle. In non-limiting aspects, of the total active ingredient loaded, the percentage of the active ingredient loaded onto the surface of the polymeric nanoparticle is between 50 and 100%, or any percent range in between, e.g., 50-90%, 60-90%, 60-80% or 70-80%. In other embodiments, the active ingredient is loaded close to the surface of the polymeric nanoparticle. In yet other embodiments, the active ingredient is loaded substantially close to the surface of the polymeric nanoparticle.

In some embodiments, an HDACi is loaded close to the surface of the polymeric nanoparticle, e.g., PLA-PEG. In other embodiments, an HDACi is loaded substantially close to the surface of the polymeric nanoparticle, e.g., PLA-PEG. In yet other aspects, an HDACi is loaded within the hydrated PEG layer. In further aspects, an HDACi is loaded within the PLA polymer phase.

Emulsification

By way of example only, some embodiments provided improved methods of manufacturing a drug delivery composition using an improved emulsion-evaporation method of nanoparticle manufacture.

Organic Solvent

Some aspects comprise forming an organic phase comprising an amphiphilic polymer and an organic solvent. In some embodiments, the organic solvent includes a water-immiscible organic solvent selected from the group consisting of DCM, chloroform, carbon tetrachloride, dichloroethane, diethyl ether, ethyl acetate, and toluene, etc. In other embodiments, the organic solvent includes water-miscible solvent mixed with water-immiscible solvents. In yet other embodiments, the water-miscible solvent is selected from the group consisting of acetaldehyde, acetic acid, acetone, acetonitrile, cyclohexane, ethanol, dimethylformamide, dioxane, heptane, hexane, methanol, formic acid, ethylamine, dimethyl sulfoxide, pentane, propanol, pyridine, and tetrahydrofuran. In certain non-limiting aspects, the organic phase is formed by combining DCM and PLA-PEG.

Pre-Emulsion Aqueous Phase

Some embodiments of the disclosure comprise combining the organic phase with a pre-emulsion aqueous phase to form a pre-emulsion mixture. In certain non-limiting embodiments, the pre-emulsion aqueous phase comprises one or more hydrophilic solvents (e.g., water).

In some embodiments, the pre-emulsion aqueous phase comprises a surfactant selected from the group consisting of sodium cholate, sodium dodecyl sulphate, poloxamer, one or more Tween® compounds, vitamin E tocopheryl polyethylene glycol succinate, and polyvinyl alcohol. Some aspects of the disclosure include dissolving the surfactant in the pre-emulsion aqueous phase using a physical force (e.g., mixing, vortexing, or shaking). Other aspects of the disclosure require no significant or material physical force for dissolving the surfactant in the pre-emulsion aqueous phase. In some aspects, the surfactant acts as an emulsifier to provide for a mixing of the organic phase and the pre-emulsion aqueous phase.

In other embodiments, the pre-emulsion aqueous phase comprises a stabilizer selected from the group consisting of sodium cholate, sodium dodecyl sulphate, poloxamer, one or more Tween® compounds, vitamin E tocopheryl polyethylene glycol succinate, and polyvinyl alcohol. Some aspects of the disclosure include dissolving the stabilizer in the pre-emulsion aqueous phase using a physical force (e.g., mixing, vortexing, or shaking). Other aspects of the disclosure require no significant or material physical force for dissolving the stabilizer in the pre-emulsion aqueous phase. In some aspects, the stabilizer acts as an emulsifier to provide for a mixing of the organic phase and the pre-emulsion aqueous phase. In yet other embodiments, the pre-emulsion aqueous phase comprises a surfactant and a stabilizer.

In certain non-limiting embodiments, the pre-emulsion aqueous phase comprises sodium cholate, TPGS or PVA. In other non-limiting embodiments, the pre-emulsion aqueous phase comprises sodium cholate.

In some embodiments, the pre-emulsion aqueous phase and the aqueous phase are prepared separately. In other embodiments, the pre-emulsion aqueous phase and the aqueous phase originate from the same aqueous solution. In further aspects, the pre-emulsion aqueous phase is mixed with the organic phase prior to emulsification, and the aqueous phase is mixed with the resulting emulsification mixture.

In certain aspects, the pre-emulsion aqueous phase and the aqueous phase are differentially modified. For example, in some embodiments, a higher concentration of surfactant is added to the pre-emulsion aqueous phase than to the aqueous phase.

Mixing the Organic Phase and the Pre-Emulsification Aqueous Phase

Some embodiments comprise mixing the organic phase and the pre-emulsion aqueous solution. For example, the pre-emulsion aqueous phase is placed in a receptacle, and a physical force (e.g., vortexing) is applied to the pre-emulsion aqueous solution. In some embodiments, while vortexing, the organic phase is added dropwise to the pre-emulsion aqueous phase until the two phases are in the same container to form the pre-emulsification mixture.

Mixing the Emulsion and the Aqueous Phase

In some aspects, the emulsion and the aqueous phase are mixed by stirring (e.g., using a stir bar on a magnetic plate). In yet other aspects, the mixture between the emulsion and the aqueous phase is stirred in an environment (e.g., a fume hood) that enables evaporation of some or all of the organic solvent. In further aspects, a vacuum is applied to facilitate evaporation of the organic solvent. In yet further aspects, thermal energy is applied to facilitate the evaporation of the organic solvent.

Adding the Active Ingredient

In certain non-limiting embodiments, the active ingredient, for example, HDACi is added to the organic phase before nanoparticles are formed through emulsification. In other embodiments, the active ingredient (e.g., HDACi) is added to the emulsion (the organic phase after nanoparticles are formed through emulsification). In yet other embodiments, for example, the active ingredient is added before removal of the organic phase (e.g., the evaporation step). In further embodiments, for example, the active ingredient is added during the evaporation step.

In some aspects, after the formation of the organic phase and preparation of the active ingredient, these two elements are combined. In some aspects, the active ingredient (e.g., HDACi) is added in a generally drop-wise manner into the organic phase. In further aspects, a physical force (e.g., vortexing) is applied to the resulting mixture to combine the active ingredient and the organic phase.

Removal of Organic Solvent

In some aspects, after removal of the organic solvent (e.g., by evaporation) and formation, the drug delivery composition is collected and washed. For example, after evaporation, the resulting mixture is filtered through a filter of desirable size (e.g., 0.22 µM) and the resulting filtrate is filtered again using filter tubes (e.g., 100 kiloDalton cut-off) and centrifugation methodologies. In some aspects, after one or more filtrations and washes, the resulting drug delivery composition is mixed with a compound (e.g., trehalose) and stored in the desired state (such as frozen or lyophilized) for storage and stability.

Emulsification

Some embodiments comprise emulsifying the pre-emulsification mixture. In some aspects, emulsification comprises a chemical, a thermal, or a mechanical action. For example, the mechanical action comprises homogenization using a blade, sonication using an ultrasonicator probe that is at least partially submerged in the pre-emulsification mixture, multiple (e.g., two or more) bursts of ultrasonication lasting several seconds, or a combination thereof. By way of example only, the bursts may last three or ten-seconds. Depending on the active ingredient, different numbers of bursts or different durations of bursts is used.

Certain non-limiting embodiments of fabricating a therapeutic nanoparticle comprising the steps of (a) preparing an aqueous phase; (b) adjusting the pH of the aqueous phase; (c) mixing an organic phase containing a polymeric nanoparticle with the aqueous phase; (d) adding a water-insoluble biologically active ingredient to the mixture; and (e) removing the organic solvent from the mixture; wherein the active ingredient having a higher water solubility in the adjusted pH than in neutral pH. In some aspects, adjusting the pH of the aqueous phase increases the electrostatic interaction between the active ingredient and the polymeric nanoparticles. In other aspects, at least 50%, at least 65%, at least 70%, at least or at least 90% of the active ingredient is ionized in the aqueous phase. In yet other aspects, the percentage of ionized active ingredient in the aqueous phase is between 50% and 100%, or any percentage in between, e.g., 50-90%, 60-90%, 60-80% or 70-80%.

Other non-limiting embodiments of fabricating a therapeutic nanoparticle comprising the steps of (a) forming an organic phase comprising an amphiphilic polymer and an organic solvent; (b) adding a biologically active ingredient having an ionizable group; (c) combining the organic phase with a pre-emulsion aqueous phase to form a pre-emulsion mixture; (d) emulsifying the pre-emulsion mixture to form an emulsion; (e) combining the emulsion with an aqueous phase; and (f) evaporating the organic solvent from the combination of the emulsion and the aqueous phase. In some embodiments, 50-100% of the active ingredient is ionized in the aqueous phase. In other embodiments, the active ingredient is added when the organic solvent is partially evaporated.

In some aspects, the active ingredient comprises an HDACi, for example, quisinostat. In other aspects, the pH of the aqueous phase is adjusted to increase the water solubility of the active ingredient. In certain non-limiting aspects, the pH of the aqueous phase is adjusted to about pH 10 (e.g., pH 9-12) to increase the water solubility of quisinostat.

In some aspects, manufacturing a HDACi-loaded therapeutic nanoparticle comprises: (a) forming an organic phase comprising a polymer (e.g., PLA-PEG) and an organic solvent (e.g., dichloromethane); (b) adding the HDACi to the organic phase; (c) forming an aqueous phase comprising a hydrophilic solvent; (d) mixing together the organic phase and a pre-emulsion aqueous phase to form an emulsification mixture; (e) emulsifying the emulsification mixture; (f) adjusting the pH of an aqueous phase to a desired pH; and mixing together the emulsification mixture with the aqueous phase. In further aspects, the method further comprises evaporating at least a portion of the organic solvent from the emulsification mixture after the addition of the aqueous phase. In some aspects, increased percent ionization of a key ionizable group increases the solubility of the HDACi. In other aspects, the ionizable group is selected from the group consisting of a hydroxamic acid group, a carboxyl group, a hydroxyl group, a sulfhydryl group, a phenolic group, an amino group, an imidazole group, a guanidinium group, a sulphonamide group, and an imide group.

As used herein, the "desired pH" refers to a pH that increases the solubility of the active ingredient (e.g., HDACi) in the aqueous phase. For example, when a compound's solubility is significantly impacted by the percent ionization of its hydroxamic acid group, the desired pH is selected from the group consisting of between pKa+0.37 and pH14 (about 70% ionization), between pKa+1 and pH14 (about 90% ionization), and between pKa+2 and pH14 (about 99% ionization). On the other hand when a compound's solubility is significantly impacted by the percent ionization of an acidic group, the desired pH is selected from the group consisting of between pH0 and pKa−0.37 (about 70% ionization), between pH0 and pKa-1 (about 90% ionization), and between pH0 and pKa+2 (about 99% ionization).

In some embodiments, manufacturing a quisinostat-loaded therapeutic nanoparticle comprises: (a) forming an organic phase comprising a polymer (e.g., PLA-PEG) and an organic solvent (e.g., dichloromethane); (b) adding quisinostat to the organic phase; (c) forming an aqueous phase comprising a hydrophilic solvent; (d) mixing together the organic phase and a pre-emulsion aqueous phase to form an emulsification mixture; (e) emulsifying the emulsification mixture; (f) adjusting the pH of an aqueous phase to about pH 10 (e.g. pH 8-14, pH 9-13, or pH 9-11); and mixing together the emulsification mixture with the aqueous phase. In further aspects, the method further comprises evaporating at least a portion of the organic solvent from the emulsification mixture after the addition of the aqueous phase. In yet further aspects, quisinostat is dissolved in a solvent, such as DMSO. In some embodiments, the aqueous solvent comprises a surfactant, for example, sodium cholate, a stabilizer, or both.

Additional Agent or Moiety

In some embodiments, the therapeutic nanoparticles further comprise an agent or a moiety. The agent is configured, for example, as a composition, a molecule, structure, or a chemical. In some aspects, the agent is used during the administration of the drug delivery system to the subject in need thereof. In other aspects, the agent is used after administration of the drug delivery system to the subject in need thereof.

Non-limiting examples of the agent include, for example, an imaging agent, a targeting agent, an agent that modifies the action or activity of the active ingredient, and a combination thereof etc.

Non-limiting examples of the targeting agent include, for example, folic acid (FA), transferrin, aptamer, epidermal growth factor receptor-targeting molecule, a peptide (e.g., a RGD peptide), and an antibody (e.g., an antibody or a portion of an antibody that targets a desired antigen), etc.

(Steichen, Caldorera-Moore et al. 2013, Bazak, Houri et al. 2015). In some aspects, the targeting agent directs the drug delivery composition, e.g., HDACi-loaded polymeric nanoparticle to a particular cell- or tissue-type, such as a tumor.

Non-limiting examples of the imaging agent include contrast medium (which absorbs or alters external electromagnetism or ultrasound) and radiopharmaceutical (which emits radiation), etc. As used herein, the term "contrast agent" refers to a substance used to increase the contrast of structures or fluids within the body in medical imaging. Non-limiting examples of the contrast agent include, for example, radiocontrast media, MRI contrast agents, and ultrasound contrast agents, etc. Radiopharmaceuticals are a group of pharmaceutical drugs which have radioactivity and can be used as diagnostic and therapeutic agents. Non-limiting examples of Radiopharmaceutical include, for example, calcium-47, carbon-11, carbon-14, chromium-51, cobalt-57, cobalt-58, erbium-169, fluorine-18, gallium-67, gallium-68, hydrogen-3, indium-111, iodine-123, iodine-125, iodine-131, iron-59, krypton-81m, nitrogen-13, oxygen-15, phosphorus-32, radium-223, rubidium-82, samarium-153, selenium-75, sodium-22, sodium-24, technetium-99m, thallium-201, xenon-133, and yttrium-90, etc. Additional, non-limiting examples of the imaging agent include, for example, a dye, a fluorophore, a radioactive-based agent, and any other imaging agents, such as quantum dots, etc. In some embodiments, the imaging agent is used to visualize the local environment.

Use of Therapeutic NPs for the Treatment of a Disorder in a Subject

In some embodiments, the active ingredient is provided in a therapeutically effective amount. In further embodiments, the drug delivery composition is administered to a subject in need thereof.

As used herein, the "therapeutically effective amount" refers to any amount of the active ingredient that treats the subject, for example, a dose or a concentration that provides a therapeutically effective amount of the active ingredient (e.g., HDACi).

The addition of a therapeutically effective amount of the active ingredient encompasses any method of dosing. Dosing of the active ingredient may include single or multiple administrations of the drug delivery composition that includes the active ingredient. Examples include administration of the drug delivery composition (e.g., once or multiple administrations) for a period of time until a diminution of the disease state is achieved, preventative treatments applied prior to the instigation of symptoms, or any other dosing regimen known in the art or yet to be disclosed that one skilled in the art would recognize as a potentially effective regimen. A final dosing regimen including the regularity of and mode of administration depends on a number of non-limiting factors such as the subject, the severity of the affliction, the route of administration, the stage of disease development, the presence of other conditions such as pregnancy, infancy, or the presence of an additional disease; or any other factor now known or yet to be disclosed.

Determination of a therapeutically effective amount of the active ingredient is within the capability of those skilled in the art, especially in light of the detailed disclosure provided herein. The effective amount of the active ingredient and/or the drug delivery composition used to affect a particular purpose as well as its toxicity, excretion, and overall tolerance may be determined in vitro, or in vivo, by pharmaceutical and toxicological procedures either known now by those skilled in the art or by any similar method yet to be disclosed. One example is the in vitro determination of the $IC_{50}$ (half maximal inhibitory concentration) of the active ingredient in cell lines or target molecules. Another example is the in vivo determination of the $LD_{50}$ (lethal dose causing death in 50% of the tested animals) of the active ingredient. The exact techniques used in determining an effective amount will depend on factors such as the type and physical/chemical properties of the active ingredient, the property being tested, and whether the test is to be performed in vitro or in vivo. The determination of an effective amount of a particular active ingredient will be well known to one of skill in the art who will use data obtained from any tests in making that determination.

As disclosed above and herein, the drug delivery system can be used to treat a disease or condition. As used herein, treatment of a condition or disease is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease. Generally, the effectiveness of treatment can be determined by comparing treated groups with non-treated groups. For example, some embodiments of the drug delivery system can be used to treat one or more forms of cancer.

Cancer cells include any cells derived from a tumor, neoplasm, cancer, pre-cancer, cell line, malignancy, or any other source of cells that have the potential to expand and grow to an unlimited degree. One or more cancer cells in the context of an organism may also be called cancer, tumor, neoplasm, growth, malignancy, or any other term used in the art to describe cells in a cancerous state.

As used herein, the subject includes any human or non-human mammal, including for example: a primate, cow, horse, pig, sheep, goat, dog, cat, or rodent, including any organisms capable of developing cancer, including human patients that are suspected of having cancer, that have been diagnosed with cancer, or that have a family history of cancer.

In some embodiments, the drug delivery composition can be administered to a subject in need thereof. For example, as provided above, the drug delivery composition can be delivered to a subject with cancer with the intention the drug delivery composition be used to treat cancer. In some embodiments, the drug delivery composition can be formed as any desirable form, including tablets, including suspension tablets, chewable tablets, effervescent tablets or caplets; pills; powders such as a sterile packaged powder, a dispensable powder, and an effervescent powder; capsules including both soft or hard gelatin capsules such as HPMC capsules; lozenges; a sachet; a sprinkle; a reconstitutable powder or shake; a troche; pellets such as sublingual or buccal pellets; granules; liquids for oral or parenteral administration (e.g., intravenous); suspensions; emulsions; semisolids; or gels. For example, in some embodiments, the drug delivery composition can be administered in a generally liquid formulation that is provided at a generally physiological pH (e.g., around 7.4).

Methodologies of manufacture provided in general accordance with some embodiments may include methods of manufacturing of a drug delivery composition. As described herein, the methods of manufacture may be considered to be significant and surprising improvements over conventional methodologies. For example, in some embodiments, the methods of manufacture provided herein may comprise a significant improvement over some common methods of manufacturing drug delivery compositions, such as polymer-based nanoparticles. In particular, the methods of manufacture provided herein may be used with and/or as a replacement for conventional methods of manufacture of polymer-based nanoparticles, such as, but not limited to the emulsion-evaporation method, the emulsion-diffusion method, the nanoprecipitation method, and the salting out method. Y. Wang et al., Nanomaterials 2016; 6, 26, which is hereby incorporated by reference in its entirety for all purposes.

As mentioned above, the modified methods of manufacture contained herein provide significant improvements over the existing methodologies. In particular, the adjustment of the pH of the aqueous phase to a generally basic pH can provide an altered physical environment, which can lead to an increased amount of active ingredient being loaded onto the forming or formed nanoparticles. Without being bound by any particular theory, it is believed that the basic pH of the aqueous phase creates an environment in which the active ingredient (e.g., any ionizable compound) is ionized prior to loading. For example, the ionized active ingredient may be generally stabilized and in equilibrium with the hydrophilic and/or hydrophobic areas of the amphiphilic polymers that form the therapeutic nanoparticles. In other aspects, it is also possible that the ionized active ingredient is generally precipitated from solution and is then bound to an exposed surface of the resulting nanoparticle.

Regardless of the theory behind the formation, as a result of the improved methodologies contained herein, the ionized active ingredient can be non-covalently bound to an exposed surface of the resulting nanoparticle. Compared to conventional systems in which the active ingredient must be loaded within the forming nanoparticle to be captured inside the nanoparticle and later delivered, this methodology results in significantly more loaded active ingredient. Specifically, the methodologies detailed herein can provide approximately 4-10 fold more loaded active ingredient compared to the conventional process.

EXAMPLES

Recent advances have highlighted the role of epigenetic aberrations in the development and progression of many cancer types, including glioblastoma (GBM) [1-6]. Histone deacetylases (HDACs) are a class of enzymes capable of producing epigenetic modification of cellular behavior. HDACs are responsible for the deacetylation of lysine residues on histones to regulate chromatin structure, transcription factor binding sites and gene expression, and their overexpression has been observed in dedifferentiated, aggres-sively proliferating tumors [7-11]. Importantly, molecules that inhibit HDACs (HDAC inhibitors, HDACis) are capable of producingapoptosis and cell cycle arrest, and they also sensitize cells to conventional DNA damaging treatments [12-16]. Currently, three first-generation HDACis are clinically approved for cutaneous T-cell lymphoma [17]. However, despite promising preclinical efficacy of first generation HDACis both in vitro and in vivo, clinical trials of HDACis have failed to show treatment benefits in solid tumors. It has been proposed that inadequate delivery and short biological halflife of most HDACis contribute to their underwhelming in vivo efficacy [18, 19]. Second generation HDACis, like quisinostat, were designedand shown to be significantly more selective and potent against class I HDACs with a longer duration of action compared to first generation HDACis, but these agents still failed to show significant efficacy as a monotherapy against solid tumors, presumably due to poor tumor delivery [18, 20]. In previous work, it has been shown that polymeric nanoparticles (NPs) can effectively encapsulate poorly water soluble small molecules to improve their tolerability in vivo and delivery to intracranial GL261 GBM tumors, which enables effective treatment of tumors after intravenous administration [21]. Importantly, Wang et al. showed the encapsulation of quisinostat within PLGA-lecithin-PEG core-shell NPs potentiated the effects of radiation in subcutaneous PC3 tumors more effectively than free drug [22]. Thus, the goal of this disclosure was to develop a formulation process that would effectively encapsulate quisinostat in NPs composed of PLA-PEG and to test whether encapsulated quisinostat would be capable of treating orthotopic GBM. Through the process of developing this drug delivery composition, the inventors identified a novel, pH-driven approach for achieving high quisinostat loading. In contrast to traditional methods that improve drug encapsulation by decreasing the aqueous solubility of the drug to drive it into the polymer core, this novel method achieves high loading by improving the solubility of quisinostat in the aqueous phase prior to solvent evaporation.

Materials

Quisinostat (JNJ-26481585) was obtained from APExBio (Houston, Tex. USA). Poly(d,l-lactide)-b-methoxy poly(ethylene glycol) (PLA-PEG, Mw~16 k:5 k Da or PLA-PEG, Mw~20 k:5 k) was purchased from PolySciTech (West Lafayette, Ind. USA). Endotoxin free (<0.0050 EU/ml) water from G-Biosciences (St. Louis, Mo. USA) was used throughout nanoparticle fabrication. Dimethyl sulfoxide (DMSO), dichloromethane (DCM), sodium cholate, 1×phosphate buffered saline (PBS), hydrochloric acid (HCl, 0.1001 M) and sodium hydroxide (NaOH, 0.1001 M) were all purchased from Sigma-Aldrich (St. Louis, Mo. USA). Dulbecco's modified Eagle medium (DMEM), fetal bovine serum (FBS), 0.25% trypsin-EDTA and geneticin selective antibiotic (G-418) were purchased from Gibco Invitrogen (Carlsbad, Calif., USA). Greiner T25 tissue culture flasks with filter cap and Costar 96-well assay plates were purchased from VWR International (Radnor, Pa., USA). Beetle luciferin (potassium salt) and CellTiter-Glo Luminescent Cell Viability Assay were purchased from Promega (Madison, Wis., UAS).

Nanoparticle Fabrication

The following steps of nanoparticle fabrication are included as an illustration only and are not intended to be limiting to the overall scope of the instant subject matter.

Nanoparticles were produced by a modified single emulsion-solvent evaporation as previously reported [21,23,24]. 50 mg PLA-PEG dissolved in 2 ml DCM was added dropwise into 4 ml of 1% (w/v) sodium cholate while vortexing, then probe sonicated (Fisher Scientific Model 705 Sonic Dismembrator, Waltham, Mass. USA) on ice in 3, 10-s bursts at 40% amplitude. The resulting emulsion was added to an evaporation phase consisting of 20 ml of 0.3% (w/v) sodium cholate (the second acqueous solution) and allowed to stir for 3 h to evaporate the DCM.

Drug Loading, Collection and Washing of Nanoparticles

Drug loaded nanoparticles were produced by adding 5 mg quisinostat, dissolved in 300 µl DMSO, dropwise into the organic phase or the evaporation phase, as specified for each formulation in Table 1. For nanoparticles made under basic or acidic conditions, the pH of the 0.3% sodium cholate evaporation phase was adjusted to the specified pH by adding dilute (0.1 M) NaOH or HCl. After the 3 h, nanoparticles were washed and concentrated through Amicon Ultra-15 Centrifugal Filters (100 kDa cut-off) for 4, 20 min spins at 5000 RCF. Aliquots were frozen and lyophilized to deter-mine thenanoparticles concentration and drug loading. The rest of thenanoparticles were frozen and stored at −80° C.

Nanoparticle Characterization

Drug Loading

Drug loading was quantified by absorbance (300 nm) on a Tecan plate reader. Lyophilized nanoparticles were dissolved at 5 mg/ml in DMSO. The nanoparticle samples were plated in triplicate (40 µl nanoparticles and 10 µl DMSO per well) in a clear, flat bottom 96-well assay plate. A control curve was constructed in technical triplicate by adding 40 µl blank nanoparticles per well and spiking with 10 µl of known drug concentrations in DMSO. Quisinostat loading was calculated as mass quisinostat/mass polymer (w/w %).

Cell Culture

GL261-LucNeo cells were generated by retroviral transduction of parent GL261 cells. The LucNeo construct (obtained from AndrewKung laboratory, Dana-Farber Cancer Institute) is described in Rubin et al. [25]. Cells were maintained under normal adherent culture conditions supplemented with G-418 as a selection pressure. Cells were grown in T25 flasks in DMEM containing glucose, L-glutamine and 10% FBS at 37° C. and 5% $CO_2$. 0.25% trypsin-EDTA was applied to collect cells, and a Cellometer mini (Nexcelom Bioscience, Lawrence, Mass. USA) was used to count cells prior to all in vitro and in vivo experiments.

In Vitro Nanoparticle Efficacy

GL261 cells were seeded in 96-well flat, white walled, clear bottom plates at a density of 3 k cells/well in 100 µl

TABLE 1

| Formulation | Quisinostat added (mg) | O/E | pH | % Loading (w/w) | Diameter (nm) | PDI | Zeta Potential (mV) |
|---|---|---|---|---|---|---|---|
| BNP | 0 | — | 7 | — | 96.3 ± 2.08 | 0.1 ± 0.01 | −13 ± 2.0 |
| QNP-1 | 5 | O | 7 | 1.3 ± 0.71 | 101 ± 2.52 | 0.1 ± 0.01 | −4.9 ± 2.3 |
| QNP-2 | 5 | O | 2 | 0.47 ± 0.25 | 103 ± 2.08 | 0.1 ± 0.01 | −6.2 ± 1.7 |
| QNP-3 | 5 | O | 10 | 5.0 ± 0.51 | 113 ± 10.0 | 0.1 ± 0.01 | −8.2 ± 0.53 |
| QNP-4 | 5 | E | 10 | 9.3 ± 0.29 | 128 ± 8.50 | 0.1 ± 0.02 | −6.0 ± 1.0 |
| QNP-5 | 5 | E | 7 | 2.7 ± 0.15 | 112 ± 2.52 | 0.1 ± 0.01 | −5.2 ± 1.7 |
| QNP-6 | 7.5 | E | 10 | 9.9 ± 0.21 | 129 ± 4.51 | 0.1 ± 0.02 | −9.8 ± 1.1 |
| QNP-7 | 10 | E | 10 | 7.7 ± 0.35 | 121 ± 2.31 | 0.1 ± 0.02 | −9.4 ± 2.1 |
| QNP-8 | 5 | E | 9 | 5.3 ± 0.12 | 115 ± 5.29 | 0.1 ± 0.01 | −8.2 ± 1.4 |
| QNP-9 | 7.5 | E | 11 | 8.9 ± 0.60 | 126 ± 3.21 | 0.1 ± 0.01 | −7.8 ± 1.6 |

Size and Zeta Potential

Nanoparticle hydrodynamic diameter and zeta potential were measured using the NanoBrook 90Plus Zeta (Brookhaven Instruments, Holtsville, N.Y. USA). All measurements were done at a nanoparticle concentration of 0.1 mg/ml in triple filtered (0.2 µm) 1 mM KCl. Reported values represent the mean±standard deviation from 3 batches unless otherwise indicated.

Transmission Electron Microscopy

Transmission electron microscopy (TEM) measurements were measured on the Phillips CM 12 operated at an accelerated voltageof 120 kV using 400 mesh formvar-coated copper grids FCF400-Cu-SB (Electron Microscopy Sciences, PA, USA). Copper-grids were first glow-discharged to increase hydrophilicity on the surface. Samples were then diluted with DI water (final concentration 4 mg/ml). Samples were prepared by pipetting 3 µl of diluted solution to the glow-discharged grids followed by ambient drying using Whatman Filter Paper (Sigma Aldrich, USA).

Controlled Release

Quisinostat release from nanoparticles was determined using a protocol adapted from Wang et al. [22]. Nanoparticles were diluted to 20 mg/ml in PBS (pH 7) and 400 µl was transferred to a 3.5 k MWCO Slide-A-Lyzer Dialysis cassette (Thermo Fisher Scientific, Waltham, Mass. USA) in triplicate. Each cassette was immersed in 2 l PBS (pH 7, replaced at each time point) at 37° C. with gentle stirring (100 rpm). At each time point, 30 µl nanoparticles was removed from the cassette and dissolved in 150 µl DMSO. 60 µl dissolved nanoparticles was added in triplicate to a clear, flat bottom, 96-well plate, and the amount of drug remaining was quantified by absorbance as described above. A free quisinostat control at the equivalent concentration was included to measure quisinostat movement across the membrane using the same protocol.

media and allowed to attach for 4 hours prior to adding treatments. Each plate was treated with 10 µl/well of 19 serial dilutions (1:2) ranging from 10 to 0 µM in PBS of either free drug or nanoparticles. After 72 hours, cell viability was assessed using CellTiter-Glo, and an $IC_{50}$ value was calculated using GraphPad Prism (San Diego, Calif. USA) by a nonlinear fit of the log (inhibitor) vs. response function.

Tumor Induction

Orthotopic GL261-LucNeo tumors were induced in C57BL/6 albino mice (Harlan Laboratories, Indianass, Ind., USA) as previously reported [23, 21]. Briefly, mice were anesthetized with anintraperitoneal injection of ketamine/xylazine (100/10 mg/kg) and mounted in a stereotaxic frame (Kopf Instruments, Tujunga, Calif., USA) on top of an infrared heating pad to maintain animal temperature. The animal's head was shaved and sterilized with three alternating passes each of betadine and ethanol. A 1 cm incision was made over midline, and a burr hole was drilled 2 mm lateral, 0.1 mm posterior of bregma. A hamiltion syringe (29 gauge needle) containing 75 k GL261-LucNeo cells in 2 µl DMEM was inserted into the hole to a depth of 2.8 mm and the cells were injected over 2 min. The needle was left in place for 1 min to reduce backflow before the wound was closed with staples. All animals received a subcutaneous (SQ) injection of Buprenorphine SR prior to surgery, and ibuprofen was provided in their water ad lib for 1 week for pain.

Tumor Growth

Bioluminescence was used to monitor and measure tumor growth as previously described [21, 23]. Imaging was done on the Xenogen IVIS Spectrum in vivo imaging system every 3-4 days starting at day 6 after tumor implantation. Mice received a SQ injection of luciferin (150 mg/kg) and were imaged 25 min post injection under 2% isoflurane. The Living Image software was used to draw an ROI around the tumor signal and measure the size of each tumor (total flux, photons/sec).

Tumor Treatment

Quisinostat-loaded nanoparticles were tested in vivo in mice bearing orthotopic GL261 tumors. After the first imaging, mice were randomly assigned to a treatment group. For the free drug study, this included saline control (100 µl) or free quisinostat (10 mg/kg IP, solubilized in 20% hydroxypropyl-β-cyclodextrin, pH 8.7). For the nanoparticle drug study, this included saline (100 µl), blank nanoparticles (BNP, 1000 mg/kg polymer), or quisinostat-loaded nanoparticles (QNP, 50 mg/kg quisinostat). One mouse in the nanoparticle study was excluded for lack of a tumor signal at the initial imaging. Mice were treated by intravenous injection (lateraltail vein) on days 11, 12, 18, and 19 post tumor induction. Treatment efficacy was measured by tumor growth and median survival. Mice were monitored daily and euthanized at the sign of symptoms (lack of grooming, abnormal gait, hunched posture, etc.) or greater than 15% weight loss.

Statistics

All statistical tests were performed using GraphPad Prism 5 software. Particle localization regions were compared using a 2-way ANOVA. Tumor growth for each treatment was compared by fitting the average growth with an exponential curve fit and comparing treatments using a one-way ANOVA. Survival differences were compared using a Kaplan-Meier curve and the Mantel-Cox test.

Results

Nanoparticle Loading and Characterization

NPs produced from amphiphilic polymers such as PLA-PEG possess a hydrophobic core, which is utilized as a favorable environment for the encapsulation of water-insoluble small molecules [26, 27]. Our initial attempts to encapsulate quisinostat in PLA-PEG NPs followed a standard single emulsion-solvent evaporation technique under neutral conditions. Quisinostat loaded NPs (QNPs) formed effectively. However, a relatively poor loading of 1.3% (Table 1, QNP-1) was achieved, which is comparable with prior reports of 2.3% (w/w) quisinostat encapsulation within PLGA-lecithin-PEG core-shell NPs [22]. Attempts were made to improve loading by varying a number of traditional formulation parameters known to affect drug loading (solvent mixtures (acetonitrile, dimethylformamide, acetone, DMSO, DCM, ethyl acetate), nanoprecipitation, feed ratios, and temperature) [28, 29]. However, none of these changes brought quisinostat loading above 2%.

In an emulsion based approach to NP formation, a hydrophobic drug is typically dissolved with the polymer in an organic solvent to aid in the encapsulation of the drug during NP formation, followed by evaporation of the solvent. The final loading of drug within the NP is thought to be determined by diffusion of drug out of the polymer core after NP formation, which is directly related to the solubility of the drug in the aqueous phase. Thus, one approach for improving loading of drug within NPs formed by emulsion is to fabricate particles under conditions that reduce drug solubility in the water phase, which is believed to drive partitioning of drug into the particle core [28, 30, 31]. Because quisinostat exhibits increased water solubility at a basic pH, it was hypothesized that acidifying the evaporation phase to pH 2 would increase quisinostat loading. However, it was observed that drug loading under acidic conditions significantly decreased compared to NPs produced under neutral conditions to 0.47% (QNP-2). As a negative control, the effect of raising the evaporation phase pH to 10 was also tested. Interestingly, a basic evaporation pH resulted in significantly higher loading compared to NP produced at pH 2 or 7, achieving a loading of 5.0% (QNP-3).

The observation that loading improves when quisinostat's aqueous solubility is increased suggests a loading mechanism that does not rely solely on hydrophobic interactions. Under basic conditions, quisinostat is expected to possess a negative charge due to deprotonation of the hydroxamic acid group, suggesting an ionic mediated loading mechanism. Since the pH was only altered after NP formation, the ionization could either enable quisinostat retention within the core of the solid NP and/or increase the stability of quisinostat at the water-polymer interface. To test whether quisinostat could be associating with the surface of the NP (as opposed to the core), blank (no drug) NPs in the primary emulsion were generated and quisinostat was added directly to the evaporation phase under basic conditions (pH 10). This formulation condition nearly doubled the effective drug incorporation over our prior attempts, achieving a quisinostat loading of 9.3% (QNP-4). Further increases to the mass of quisinostat added to the aqueous phase, from 5 mg to 7.5 or 10 mg, did not result in increased loading (QNP-6 and QNP-7) even at ahigher pH (pH 11, QNP-9), supporting a saturable association of drug with the surface of the NP. Formulations at a pH 7 or pH 9, while following an identical post-loading procedure, NP loading dropped to 2.7% (QNP-5) and 5.3% (QNP-8), respectively. When the organic phase (DCM) was pre-evaporated prior to addition of quisinostat, with or without pH change, NP loading dropped to <3% (data not shown). Thus, the highest effective loading of quisinostat (QNP-4) requires the deprotonation of quisinostat at a pH above 10 and can be achieved after NPs are formed but only in the presence of organic solvent. The increase in quisinostat loading as pH increases up to pH 10 with no increase seen at pH 11 supports an ionic association with the full ionization of quisinostat occurring between pH 9 and 10.

Figure 2:
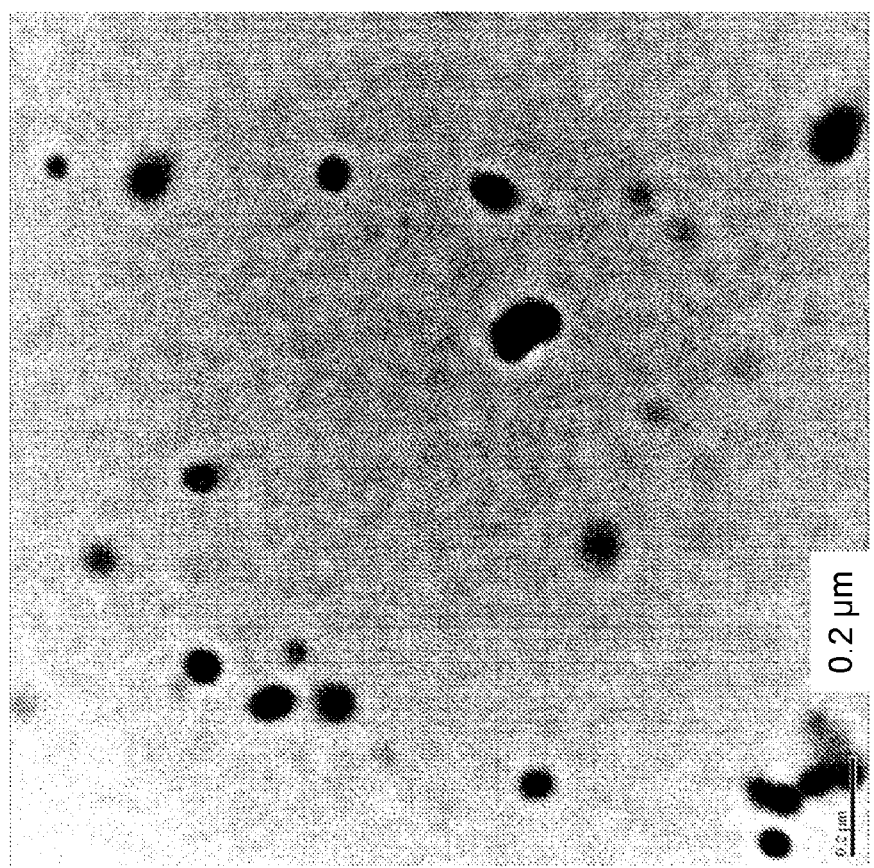
FIG. 2 depicts QNPs imaged by TEM. QNPs appeared spherical, and their ~100 nm size is consistent with DLS measurements. No evidence of drug precipitates in the samples was observed. Scale bar=0.2 μm.

One experimental concern is whether the loading measured in these experiments could reflect drug precipitates instead of NP-associated drug. There are three pieces of evidence that contradict this possibility. First, the optical quality of the emulsion is characteristic of ultra-small polymeric nanoparticles, possessing a translucent/blue hue that is not observed when drug precipitates [32]. Second, TEM characterization does not show drug precipitates (FIG. 2). Third, when PLA-PEG was excluded but post-loading fabrication conditions otherwise maintained, only 10 µg of quisinostat was recovered.

Figure 3:
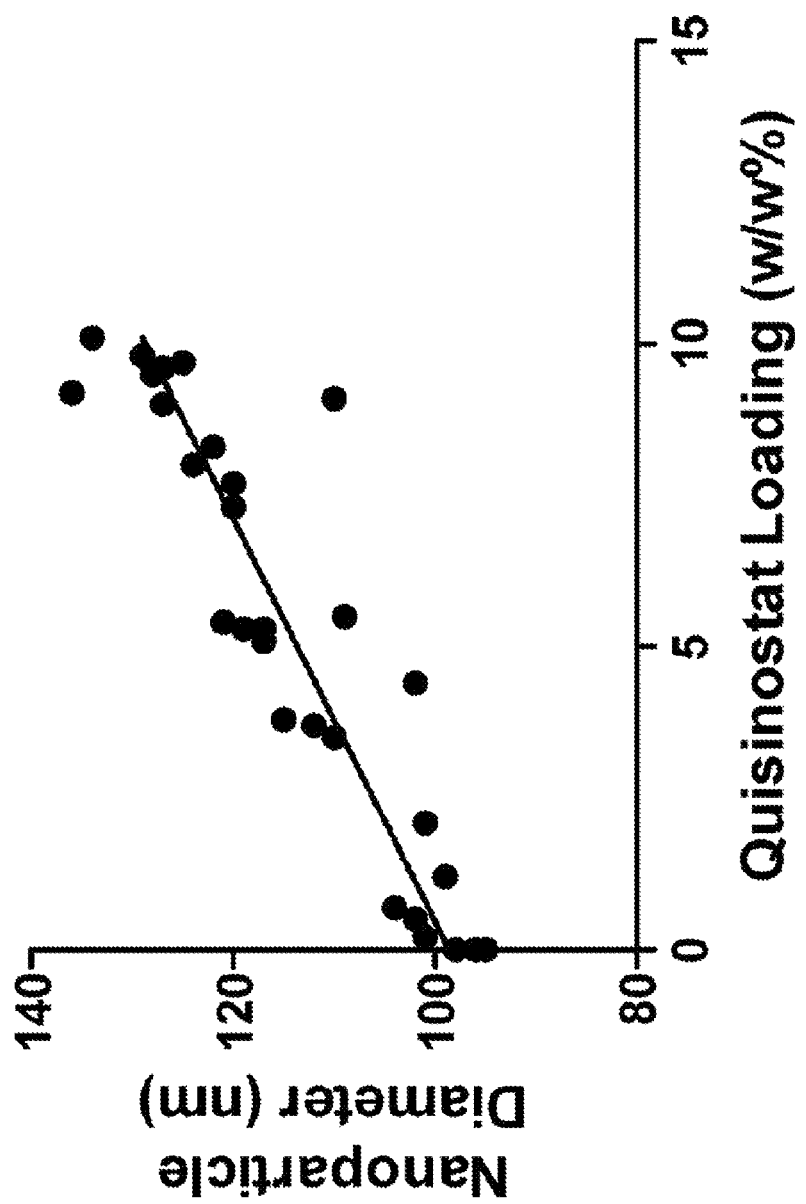
FIG. 3 depicts the correlation between Nanoparticle size and quisinostat loading. Nanoparticle's hydrodynamic diameter, as measured by DLS, positively correlated (Pearson coefficient=0.9108, p<0.0001) with the quisinostat loading for each batch. Each data point represents an individual batch.

Each NP formulation was also characterized by DLS to measure size and zeta potential. BNPs formed by our standard technique (neutral pH evaporation phase) possessed an average diameter of 96 nm and a zeta potential of −13 mV (Table 1). Alterations to the evaporation phase pH did not significantly alter the biophysical properties of BNPs (data not shown). The presence of quisinostat resulted in NPs with a slightly more neutral surface charge compared to NPs lacking quisinostat, but the amount of quisinostat loaded did not significantly affect the surface charge across QNP formulations. In contrast, the measured NP diameters positively correlated with quisinostat loading, with the average diameter increasing to 129 nm for the formulation with the highest loading (FIG. 3). This phenomenon is consistent with previous reports showing increased NP diameter when drugs are loaded onto the surface of polymeric NPs [33, 34]. These observations further support the drug loading measured represents NP-associated quisinostat, as opposed to precipitated drug.

Figure 4:
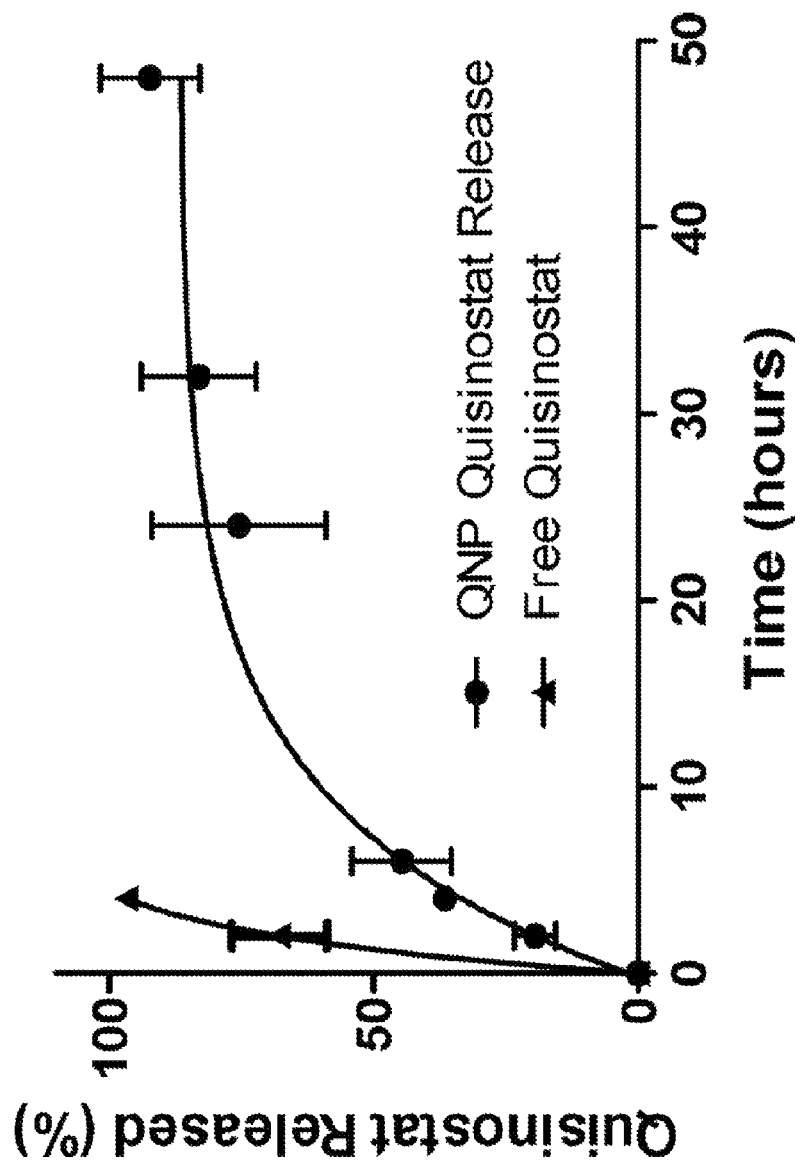
FIG. 4 depicts in vitro quisinostat release from QNPs. QNPs released quisinostat into PBS at 37° C. over 48 h, with nearly 50% release occurring in the first 6 h. Free quisinostat was completely released from the cassette within 4 h. Points and error bars represent the mean+SD of 3 samples read in triplicate at each time point.

Quisinostat release from QNPs or as free drug at 37° C. in PBS was measured by absorbance after 1, 2, 4, 6, 24, 32, and 48 h. Free quisinostat was completely released from the dialysis cassette by 4 h, whereas only 50% of quisinostat was released from NPs after 6 h, and complete NP release was achieved by 48 h (FIG. 4). The fast rate of release from PLA-PEG NPs is in contrast to the 5 days of sustained release previously reported for quisinostat encapsulated within the core of PLGA-lipid hybrid NPs [22]. A rapid burst release supports surface loading of quisinostat [34, 35], and the subsequent phase of sustained release is presumably due to electrostatic interactions with the particle, which have previously been demonstrated to enable the sustained release of proteins from PLGA NPs, even in absence of encapsulation [36]. It remains to be determined whether quisinostat resides within the hydrated PEG layer or is within the PLA polymer phase and merely close to the surface. It is not immediately clear that the burst release is a problem for quisinostat drug delivery, since NPs typically distribute and clear over similar time frames to the release kinetics observed here [37, 38].

The data demonstrate that the pH of the aqueous phase is a major force driving quisinostat loading into or onto PLA-PEG NPs formed by emulsion, and suggest that the mechanism is charge-mediated. A likely possibility is that the deprotonation of quisinostat under basic conditions increases NP loading due to electrostatic interactions. Presumably, the presence of the organic solvent is required to achieve this because it enhances overall solubility of the drug to enable this interaction. Previous works have described the loading of drugs and proteins onto the surface of inorganic [39, 40] and polymeric [34-36] NPs. These effects have been reported to be a function of charge interactions, [34-37] and their pH-dependency supports ionization as a primary mechanism [34, 36, 39, 40]. Additionally, a charge-dependent loading of proteins onto the surface of PLGA has been demonstrated in a post-fabrication scheme [36]. However, to our knowledge, similar approaches have not yet been demonstrated for loading small molecules on PLA-PEG, and have also not been reported for HDACis.

QNP Activity and Efficacy

Figure 5:
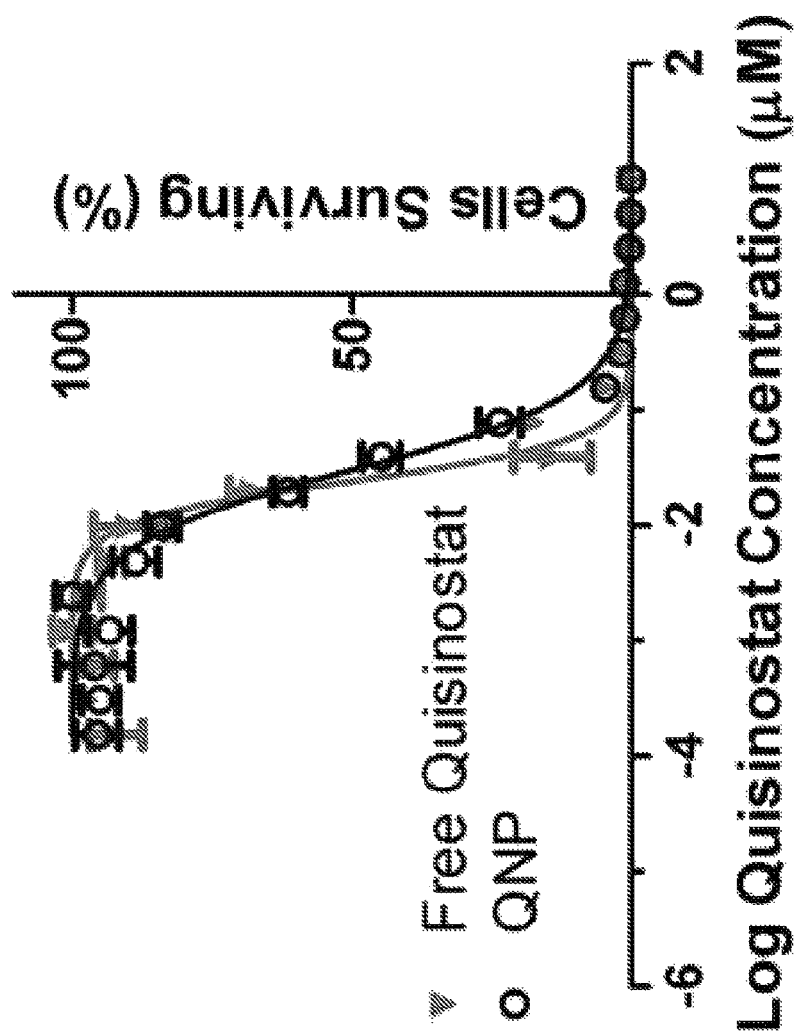
FIG. 5 depicts in vitro QNP efficacy against GL261. QNP and free quisinostat exhibited equipotent growth inhibition against GL261 murine glioma cells in vitro with IC50s of 30 and 24 nM, respectively. Points and error bars represent the mean±SD of 3 samples read in triplicate at each dilution.

To test whether quisinostat potency is maintained after NP loading, growth inhibition produced by free versus NP quisinostat in vitro was evaluated in GL261 cultures. Both free and NP-loaded quisinostat effectively inhibited the growth of GL261 cells with IC50 values of 24 and 30 nM, respectively (FIG. 5). No significant changes in quisinostat potency due to the NP loading process were found, and the low nanomolar IC50 is consistent with reported quisinostat IC50 values against other glioblastoma cell lines [19].

Multiple investigators have identified HDAC inhibitors as drugs of interest for treating cancer, including GBM [1, 8, 17, 41-43]. While in vitro results have been promising, little success has been observed in vivo [20, 44, 45]. As a monotherapy, quisinostat and other HDIs have shown the greatest in vivo efficacy against hematological cancers [17, 19, 46]. Against solid tumors, HDIs are most commonly utilized as a combination therapy to achieve efficacy [6, 20, 22, 47]. Although the mechanism for the in vivo failure of quisinostat or other HDIs as a monotherapy is unknown, it has been suggested that poor delivery may be a factor. NPs have the potential to improve in vivo efficacy of systemically administered agents through a variety of mechanisms, including improved solubility (enabling a higher dose to be delivered), enhanced permeation and retention (EPR) in leaky tumor vasculature, and/or alteration to pharmacokinetic profile of free drug. For example, in previous work, a NP encapsulation strategy was utilized to deliver the otherwise ineffective drug camptothecin (CPT) to intracranial GBM [21]. CPT is a potent drug in cell culture but is very poorly water soluble, inactivated at physiological pH, and cleared rapidly following systemic administration. Encapsulation of CPT within poly(lactic-co-glycolic acid) (PLGA) NPs improved drug tolerability dramatically, which produced a robust slowing of tumor growth and prolongation of survival in mice bearing intracranial tumors. Based on this previous work, it was predicted that NP encapsulation would provide a similar benefit to the action of quisinostat.

Figure 6:
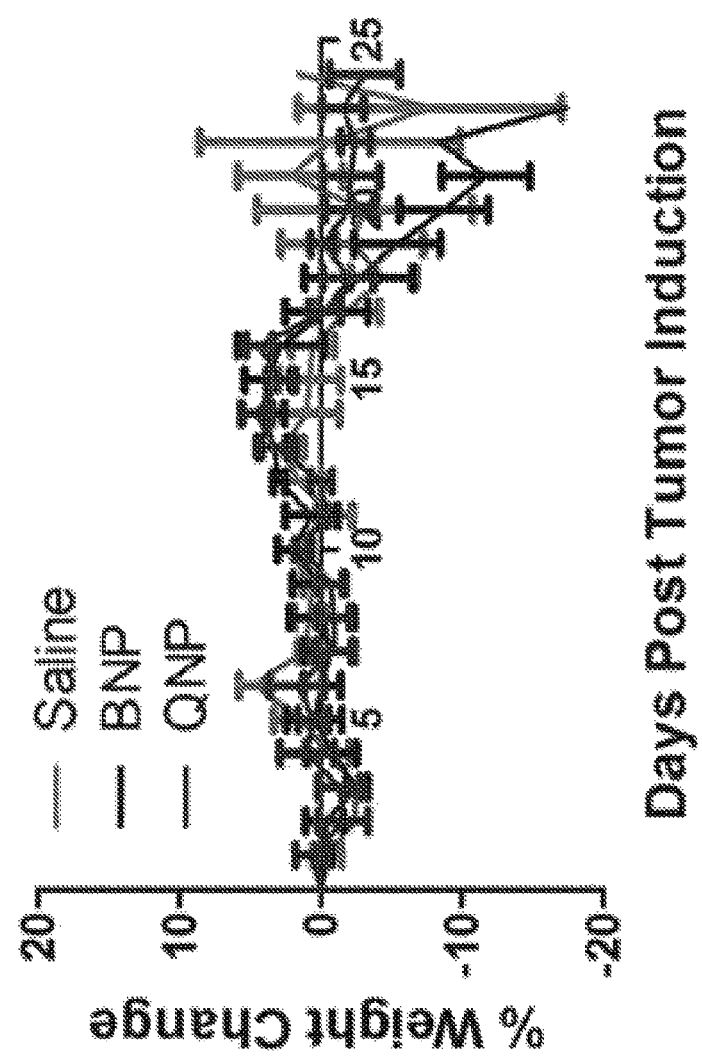
FIG. 6. Mice receiving QNP treatment showed similar weight fluctuations over the course of treatments as control mice. Control treated mice weight remained steady until the tumor burden became too great. Error bars indicate mean±SD (n=3-4 mice/treatment).

Prior works using hydroxy-propyl-β-cyclodextrin and/or mannitol to solubilize quisinostat for injection report the maximum tolerated dose to be in the range of 35-70 mg/kg/week when administered by IP or SQ injection [18, 19, 46]. In these studies, mice did not show significant weight loss at QNP doses up to 100 mg quisinostat/kg/week IV (FIG. 6), suggesting an improvement in quisinostat tolerability after NP encapsulation. Quisinostat has previously shown efficacy against subcutaneous GBM xenografts [19], which confirms quisinostat demonstrates expected activity against GBM but does not address delivery barriers related to orthotopic tumors. Treatment of orthotopic GBM is significantly hindered by the blood-brain barrier (BBB), which presents both active and passive barriers to restrict the entry of chemotherapies [48, 49]. Nearly all drugs of interest for GBM fail to achieve adequate tumor concentrations at a safe dose [50]. Thus, the inability of subcutaneous tumors to recapitulate these unique drug delivery challenges makes intracranial GBM models necessary for evaluating treatment efficacy.

Figure 7:
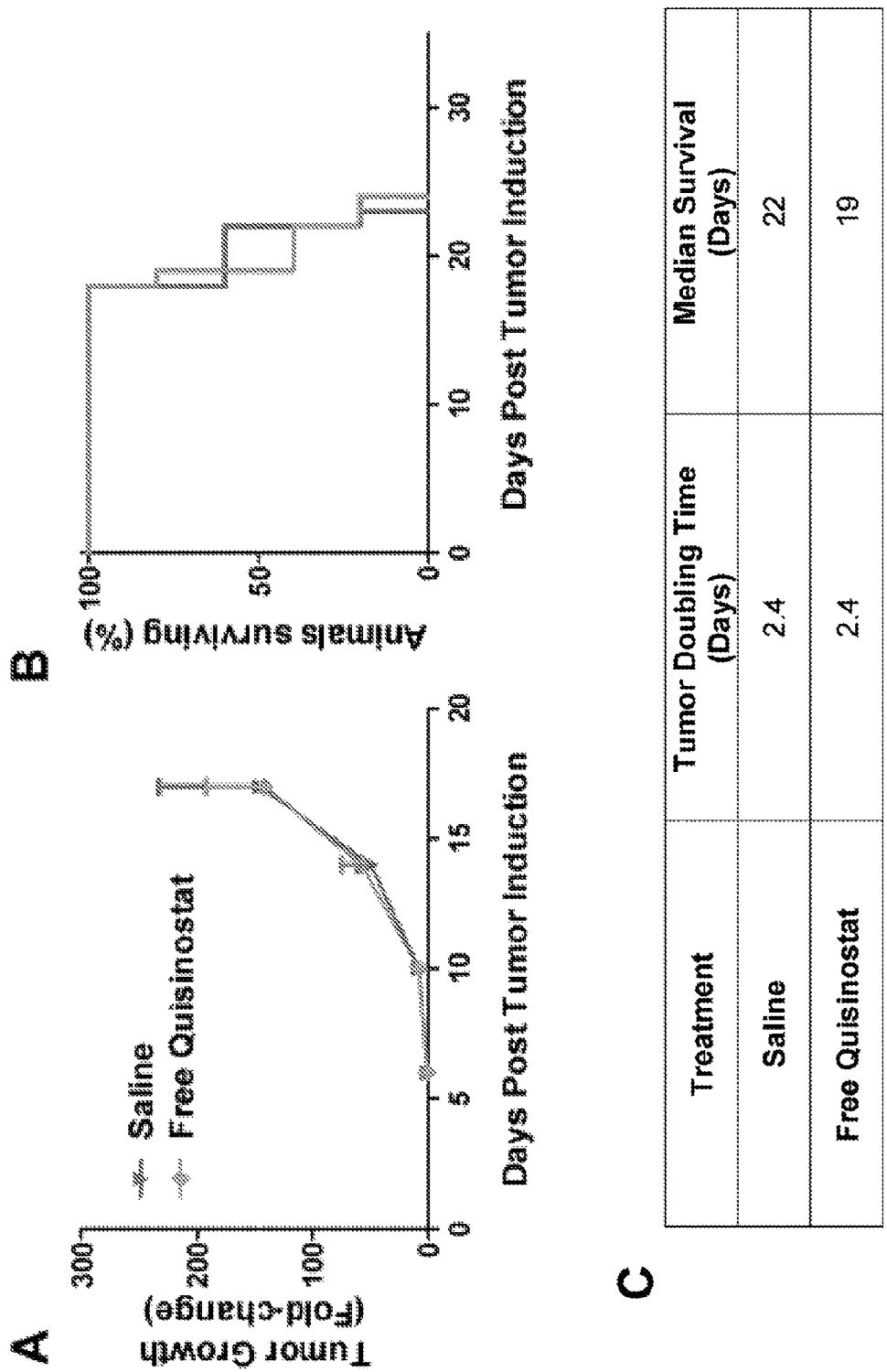
FIG. 7 depicts free quisinostat treatment efficacy in mice bearing orthotopic GL261 tumors. (A) Tumor growth was determined by the change in tumor size (mean±SD) from day 6, as measured by bioluminescence. (B) Survival is shown on the Kaplan-Meier plot. (C) Saline (n=5) and Free Quisinostat (n=5) treated tumors both doubled in size every 2.4 days and had median survival times of 22 and 19 days, respectively.
Figure 8:
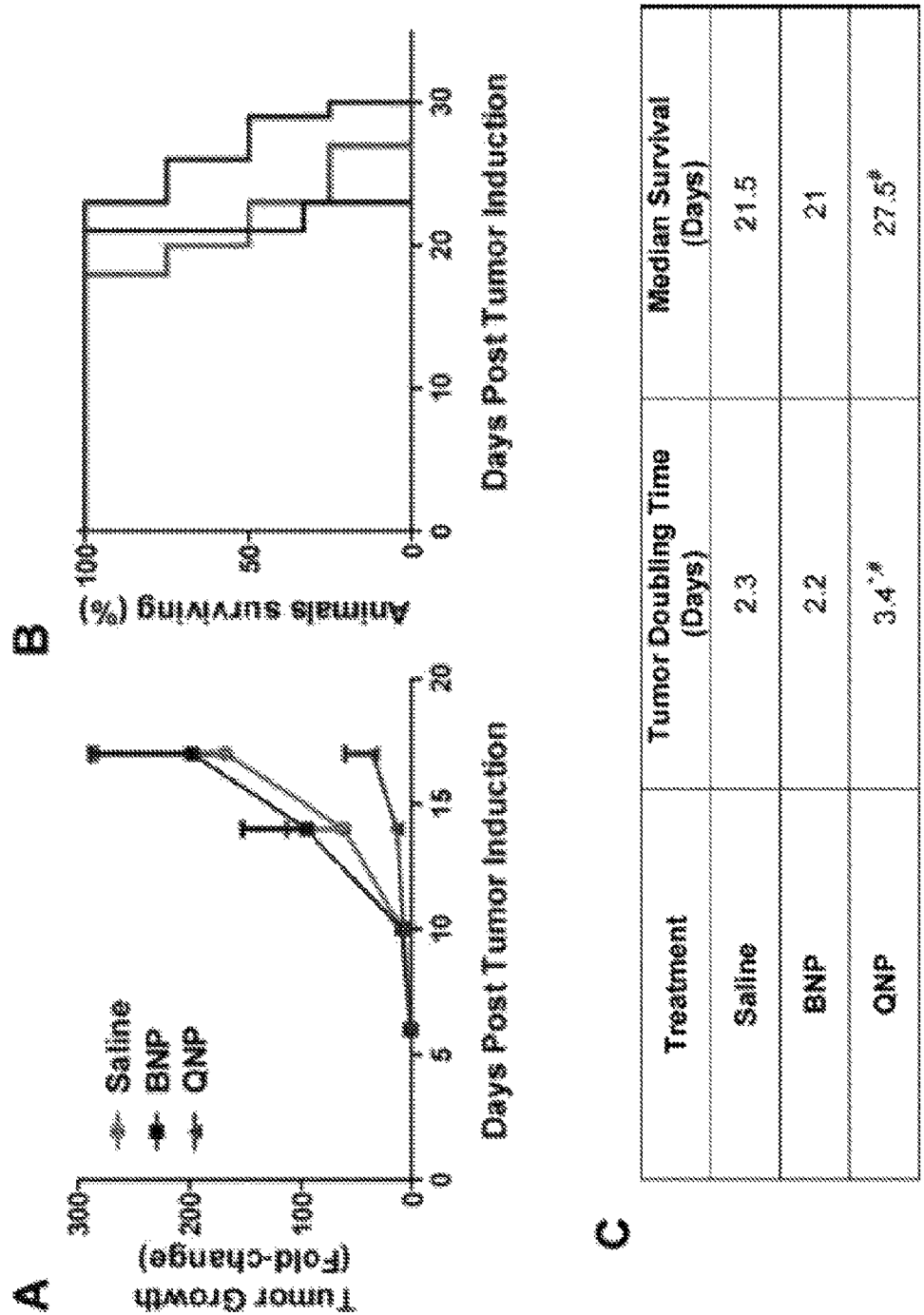
FIG. 8. QNP in vivo treatment efficacy in mice bearing orthotopic GL261 tumors. (A) Tumor growth determined by the change in tumor size (mean±SD) from day 6 as measured by bioluminescence. (B) Survival is shown on the Kaplan-Meier plot. (C) Saline (n=4) and BNP (n=3) treated tumors grew exponentially and had median survival times of 21.5 and 21 days, respectively. QNP (n=4) treatment significantly slowed tumor doubling compared to both controls, leading to the significantly prolonged survival of 27.5 days compared to BNP treatment. # designates significance (p<0.05) compared to BNP. designates significance (p<0.05) compared to saline. Statistical testing on tumor doubling time was performed with a one-way ANOVA followed by Tukey post-hoc testing. Statistical testing on survival was performed by the Mantel-Cox test.

To test whether free quisinostat could treat an orthotopic tumor, intracranial GL261-LucNeo tumors were induced in 10 C57BL/6 albino mice and treated with either saline or free quisinostat (n=5/group) by IP injection on days 11, 12, 18, and 19. Free quisinostat failed to provide any treatment benefit with a tumor doubling time of 2.4 days for both treatment and a median survival of 22 and 19 days for saline and quisinostat, respectively (FIG. 7). In a separate cohort of 12 mice bearing intracranial tumors, the subjects were divided into 3 treatment groups (saline, BNPs or QNPs) and treatments were administered IV by lateral tail vein injection on days 11, 12, 18, and 19. Tumor growth was exponential in both saline and BNP treated mice with an average tumor doubling time of 2.3 and 2.2 days, respectively, while QNPs significantly ($p<0.05$) slowed the tumor doubling time, to 3.4 days (FIG. 8). This delay in tumor growth resulted in a significant increase in median survival to 27.5 days for QNP treated compared to 21 days for those treated with BNPs ($p=0.03$) and tended to prolong survival compared to the 21.5 days for saline treated mice ($p=0.10$). Although a modest improvement in survival, these data show NP encapsulation of quisinostat can improve its tolerability and efficacy over free drug to effectively slow intracranial GBM growth as a monotherapy.

This disclosure presents a novel pH driven approach for achieving high quisinostat loading of PLA-PEG NPs, □9% (w/w), after NP formation. In contrast to the typical approach of reducing drug solubility in the aqueous phase to drive partitioning of drug into the NP core, the data show that quisinostat loading increases as its aqueous solubility increases, which likely is due to a charge-mediated association of drug with the nanoparticle surface. QNPs produced by these methods effectively release drug over 48 h and possess equivalent activity to free drug in vitro. Additionally, QNPs were found to robustly slow orthotopic GL261 tumor growth and prolong survival compared to control treated mice. These data support a novel mechanism for loading NPs with quisinostat and further the development of HDACis for the treatment of orthotopic glioblastoma.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this disclosure as defined in the claims appended hereto.

REFERENCES

[1] C. Damaskos, S. Valsami, M. Kontos, E. Spartalis, T. Kalampokas, E. Kalampokas, A. Athanasiou, D. Moris, A. Daskalopoulou, S. Davakis, G. Tsourouflis, K. Kontzoglou, D. Perrea, N. Nikiteas, D. Dimitroulis, Histonedeacetylase inhibitors: an attractive therapeutic strategy against Breast cancer, Anticancer Res. 37 (2017) 35-46.

[2] A. A. Lane, B. A. Chabner, Histone deacetylase inhibitors in cancer therapy, J. Clin. Oncol. 27 (2009) 5459-5468.

[3] C. A. Lopez, F. Y. Feng, J. M. Herman, M. K. Nyati, T. S. Lawrence, M. Ljungman, Phenylbutyrate sensitizes human glioblastoma cells lacking wild-type p53 function to ionizing radiation, Int. J. Radiat. Oncol. Biol. Phys. 69 (2007) 214-220.

[4] M. Entin-Meer, X. Yang, S. R. VandenBerg, K. R. Lamborn, A. Nudelman, A. Rephaeli, D. A. Haas-Kogan, In vivo efficacy of a novel histone deacetylaseinhibitor in combination with radiation for the treatment of gliomas, Neuro-oncology 9 (2007) 82-88.

[5] H. C. Ugur, N. Ramakrishna, L. Bello, L. G. Menon, S.-K. Kim, P. M. Black, R. S. Carroll, Continuous intracranial administration of suberoylanilidehydroxamic acid (SAHA) inhibits tumor growth in an orthotopic gliomamodel, J. Neurooncol. 83 (2007) 267-275.

[6] C. Zagni, G. Floresta, G. Monciino, A. Rescifina, The search for potent, small-molecule HDACIs in cancer treatment: a decade after vorinostat, Med. Res. Rev. (2017).

[7] B. Campos, J. L. Bermejo, L. Han, J. Felsberg, R. Ahmadi, N. Grabe, G. Reifenberger, A. Unterberg, C. Herold-Mende, Expression of nuclear receptor corepressors and class I histone deacetylases in astrocytic gliomas, Cancer Sci. 102 (2011) 387-392.

[8] E. Ceccacci, S. Minucci, Inhibition of histone deacetylases in cancer therapy: lessons from leukaemia, Br. J. Cancer 114 (2016) 605-611.

[9] M. Dvorakova, T. Vanek, Histone deacetylase inhibitors for the treatment of cancer stem cells, Med. Chem. Commun. 7 (2016) 2217-2231.

[10] F. S. Giudice, D. S. P Jr., J. E. Nör, C. H. Squarize, R. M. Castilho, Inhibition of histonedeacetylase impacts cancer stem cells and induces epithelial-mesenchymetransition of head and neck cancer, PLoS One 8 (2013) e58672.

[11] M. Cornago, C. Garcia-Alberich, N. Blasco-Angulo, N. Vall-llaura, M. Nager, J. Herreros, J. X. Comella, D. Sanchis, M. Llovera, Histone deacetylase inhibitorspromote glioma cell death by G2 checkpoint abrogation leading to mitoticcatastrophe, Cell. Death. Dis. 5 (2014) e1435.

[12] L. Zhu, K Wu, S. Ma, S. Zhang, HDAC inhibitors: a new radiosensitizer for non-small-cell lung cancer, Tumori 101 (2015) 257-262.

[13] Y. Imai, Y. Maru, J. Tanaka, Action mechanisms of histone deacetylase inhibitors in the treatment of hematological malignancies, Cancer Sci. 107 (2016) 1543-1549.

[14] J.-M. Shieh, Y.-A. Tang, F.-H. Hu, W.-J. Huang, Y.-J. Wang, J. Jen, S.-Y. Liao, Y.-H. Lu, Y.-L. Yeh, T.-W. Wang, P. Lin, Y.-C. Wang, A histone deacetylase inhibitorenhances expression of genes inhibiting Wnt pathway and augments activity of DNA demethylation reagent against nonsmall-cell lung cancer, Int. J. Cancer. 140 (2017) 2375-2386.

[15] A. Newbold, K. J. Falkenberg, H. M. Prince, R. W. Johnstone, How do tumor cells respond to HDAC inhibition? FEBS J. 283 (2016) 4032-4046.

[16] H. S. Rugo, N. Vidula, C. Ma, Improving response to hormone therapy in Breastcancer: new targets, new therapeutic options, Am. Soc. Clin. Oncol. Educ. BookAm. Soc. Clin. Oncol. Meet. 35 (2016) e40-54.

[17] M. Mottamal, S. Zheng, T. L. Huang, G. Wang, Histone deacetylase inhibitors inclinical studies as templates for new anticancer agents, Mol. Basel Switz. 20 (2015) 3898-3941.

[18] J. Arts, P. King, A. Marien, W. Floren, A. Belien, L. Janssen, I. Pilatte, B. Roux, L. Decrane, R. Gilissen, I. Hickson, V. Vreys, E. Cox, K. Bol, W. Talloen, I. Goris, L. Andries, M. D. Jardin, M. Janicot, M. Page, K. van Emelen, P. Angibaud, a novel second-generation oral histone deacetylase inhibitor shows broad-spectrum preclinical antitumoral activity, Am. Assoc. Cancer Res. 15 (2009) 6841-6851.

[19] H. Carol, R. Gorlick, E. A. Kolb, C. L. Morton, D. M. Manesh, S. T. Keir, C. P. Reynolds, M. H. Kang, J. M. Maris, A. Wozniak, I. Hickson, D. Lyalin, R. T. Kurmasheva, P. J. Houghton, M. A. Smith, R. Lock, Initial testing (Stage 1) of the histone deacetylase inhibitor, quisinostat (JNJ-26481585), by the pediatric preclinical testing program, pediatr, Blood Cancer 61 (2014) 245-252.

[20] B. Venugopal, R. Baird, R. S. Kristeleit, R. Plummer, R. Cowan, A. Stewart, N. Fourneau, P. Hellemans, Y. Elsayed, S. Mcclue, J. W. Smit, A. Forslund, C. Phelps, J. Camm, T. R. J. Evans, J. S. de Bono, U. Banerji, A phase I study of quisinostat (JNJ-26481585), an oral hydroxamate histone deacetylase inhibitor with evidence of target modulation and antitumor activity, in patients with advanced solid tumors, Clin. Cancer Res. 19 (2013) 4262-4272.

[21] K. T. Householder, D. M. DiPerna, E. P. Chung, G. M. Wohlleb, H. D. Dhruv, M. E. Berens, R. W. Sirianni, Intravenous delivery of camptothecin-loaded PLGA nanoparticles for the treatment of intracranial glioma, Int. J. Pharm. 479 (2015) 374-380.

[22] E. C. Wang, Y. Min, R. C. Palm, J. J. Fiordalisi, K. T. Wagner, N. Hyder, A. D. Cox, J. Caster, X. Tian, A. Z. Wang, Nanoparticle formulations of histone deacetylaseinhibitors for effective chemoradiotherapy in solid tumors, Biomaterials 51 (2015) 208-215.

[23] R. L. Cook, K. T. Householder, E. P. Chung, A. V. Prakapenka, D. M. DiPerna, R. W. Sirianni, A critical evaluation of drug delivery from ligand modified nanoparticles: confounding small molecule distribution and efficacy in thecentral nervous system, J. Control. Release 220 (2015) 89-97.

[24] Y. Deng, J. K. Saucier-Sawyer, C. J. Hoimes, J. Zhang, Y.-E. Seo, J. W. Andrejecsk, W. M. Saltzman, The effect

[25] J. B. Rubin, A. L. Kung, R. S. Klein, J. A. Chan, Y. Sun, K. Schmidt, M. W. Kieran, A. D. Luster, R. A. Segal, A small-molecule antagonist of CXCR4 inhibits intracranial growth of primary brain tumors, Proc. Natl. Acad. Sci. 100 (2003) 13513-13518.

[26] K. Letchford, H. Burt, A review of the formation and classification of amphiphilic block copolymer nanoparticulate structures: micelles, nanospheres, nanocapsules and polymersomes, Eur, J. Pharm. Biopharm. 65 (2007) 259-269.

[27] K. Avgoustakis, Pegylated poly(lactide) and poly(lactide-co-glycolide) nanoparticles: preparation, properties and possible applications in drugdelivery, Curr. Drug Deliv. 1 (2004) 321-333.

[28] Y. Zhang, T. Ren, J. Gou, L. Zhang, X. Tao, B. Tian, P. Tian, D. Yu, J. Song, X. Liu, Y. Chao, W. Xiao, X. Tang, Strategies for improving the payload of small molecular drugs in polymeric micelles, J. Control. Release 261 (2017) 352-366.

[29] S. K. Adesina, U. Ezeonyebuchi, E. O. Akala, The effect of formulation variables on drug loading of antitubercular drugs in nanoparticle formulations, Mater. Res. Express. 2 (2015).

[30] L. Peltonen, J. Aitta, S. Hyvonen, M. Karjalainen, J. Hirvonen, Improved entrapment efficiency of hydrophilic drug substance during nanoprecipitation of poly(I)lactide nanoparticles, AAPS PharmSciTech 5 (2004).

[31] Y. Wang, P. Li, L. Kong, Z. Peng, Y. Luo, Formulation optimization for high drug loading colonic drug delivery carrier, 2010 3rd Int Conf. Biomed. Eng. Inform. (2010) 1686-1689.

[32] R. L. McCall, R. W. Sirianni, PLGA nanoparticles formed by single- or double-emulsion with vitamin E-TPGS, J. Vis. Exp. 51015 (2013).

[33] T. Govender, S. Stolnik, M. C. Garnett, L. Illum, S. S. Davis, PLGA nanoparticles prepared by nanoprecipitation: drug loading and release studies of a water soluble drug, J. Control. Release 57 (1999) 171-185.

[34] A. A. Lozano-Perez, H. C. Rivero, M. del, C. Pérez Hernández, A. Pagán, M. G. Montalbán, G. Villora, J. L. Cénis, Silk fibroin nanoparticles: efficient vehicles for the natural antioxidant quercetin, Int. J. Pharm. 518 (2017) 11-19.

[35] N. Brasseur, D. Brault, P. Couvreur, Adsorption of hematoporphyrin ontopolyalkylcyanoacrylate nanoparticles: carrier capacity and drug release, Int. J. Pharm. 70 (1991) 129-135.

[36] M. M. Pakulska, I. Elliott Donaghue, J. M. Obermeyer, A. Tuladhar, C. K. McLaughlin, T. N. Shendruk, M. S. Shoichet, Encapsulation-free controlledrelease: electrostatic adsorption eliminates the need for protein encapsulation in PLGA nanoparticles, Sci. Adv. 2 (2016).

[37] L. Crawford, J. Higgins, D. Putnam, A simple and sensitive method to quantify biodegradable nanoparticle biodistribution using europium chelates, Sci. Rep. 5 (2015).

[38] P. Rafiei, A. Haddadi, Docetaxel-loaded PLGA and PLGA-PEG nanoparticles for intravenous application: pharmacokinetics and biodistribution profile, Int. J. Nanomed. 12 (2017) 935-947.

[39] R. Mejias, R. Costo, A. G. Roca, C. F. Arias, S. Veintemillas-Verdaguer, T. González-Carre~no, M. del Puerto Morales, C. J. Serna, S. Ma~nes, D. F. Barber, Cytokine adsorption/release on uniform magnetic nanoparticles for localized drug delivery, J. Controlled Release 130 (2008) 168-174.

[40] D. Curry, A. Cameron, B. MacDonald, C. Nganou, H. Scheller, J. Marsh, S. Beale, M. Lu, Z. Shan, R. Kaliaperumal, H. Xu, M. Servos, C. Bennett, S. MacQuarrie, K. D. Oakes, M. Mkandawire, X. Zhang, Adsorption of doxorubicin oncitrate-capped gold nanoparticles: insights into engineering potent chemotherapeutic delivery systems, Nanoscale 7 (2015) 19611-19619.

[41] E. Adamopoulou, U. Naumann, HDAC inhibitors and their potential applications to glioblastoma therapy, Oncoimmunology 2 (2013).

[42] B. E. Gryder, Q. H. Sodji, A. K. Oyelere, Targeted cancer therapy: giving histonedeacetylase inhibitors all they need to succeed, Future Med. Chem. 4 (2012) 505-524.

[43] E. Hornig, M. V. Heppt, S. A. Graf, T. Ruzicka, C. Berking, Inhibition of histonedeacetylases in melanoma—a perspective from bench to bedside, Exp. Dermatol. 25 (2016) 831-838.

[44] F. El Bahhaj, I. Denis, L. Pichavant, R. Delatouche, F. Collette, C. Linot, D. Pouliquen, M. Grégoire, V. Héroguez, C. Blanquart, P. Bertrand, Histonedeacetylase inhibitors delivery using nanoparticles with intrinsic passive tumor targeting properties for tumor therapy, Theranostics 6 (2016) 795-807.

[45] M. S. Gilardini Montani, M. Granato, C. Santoni, P. Del Porto, N. Merendino, G. D'Orazi, A. Faggioni, M. Cirone, Histone deacetylase inhibitors VPA and TSA induce apoptosis and autophagy in pancreatic cancer cells, Cell. Oncol. Dordr. 40 (2017) 167-180.

[46] S. Deleu, M. Lemaire, J. Arts, E. Menu, E. Van Valckenborgh, P. King, I. VandeBroek, H. De Raeve, B. Van Camp, P. Croucher, K. Vanderkerken, The effects of a novel hydroxamate-based histone deacetylase inhibitor, on the development of multiple myeloma in the 5T2MM and 5T33MM murinemodels, Leukemia 23 (2009) 1894-1903.

[47] S. Deleu, M. Lemaire, J. Arts, E. Menu, E. V. Valckenborgh, I. V. Brock, H. D. Raeve, L. Coulton, B. V. Camp, P. Croucher, K. Vanderkerken, Bortezomib alone or in combination with the histone deacetylase inhibitor JNJ-26481585: effect on myeloma bone disease in the 5T2MM murine model of myeloma, Cancer Res. 69 (2009) 5307-5311.

[48] A. Bhowmik, R. Khan, M. K. Ghosh, Blood brain barrier: a challenge for effectual therapy of brain tumors, BioMed Res. Int. 2015 (2015).

[49] M. S. Lesniak, H. Brem, Targeted therapy for brain tumours, Nat. Rev. DrugDiscov. 3 (2004) 499-508.

[50] W. P. Mason, Blood-brain barrier-associated efflux transporters: a significant but underappreciated obstacle to drug development in glioblastoma, Neuro-oncology 17 (2015) 1181-1182.

What is claimed is:

1. A method of fabricating a therapeutic nanoparticle formulation, comprising:
   a. preparing an aqueous phase;
   b. adjusting the pH of the aqueous phase;
   c. mixing an organic phase with the aqueous phase, wherein the organic phase comprises an organic solvent and a nanoparticle comprising an amphiphilic polymer, wherein the amphiphilic polymer is selected from the group consisting of poly(lactic acid)-poly(ethylene glycol) (PLA-PEG), poly(lactic-co-glycolic acid)-poly(ethylene glycol), poly(lactic-co-glycolic acid)-d-α-tocopheryl polyethylene glycol succinate, poly(lactic-coglycolic acid)-ethylene oxide fumarate, poly(glycolic acid)-poly(ethylene glycol), polycaprolactone-poly(ethylene glycol), and a combination thereof;

d. partially removing the organic solvent to drive nanoparticle formation; and e. after step (d), adding a water-insoluble biologically active ingredient in the presence of remaining organic solvent to form the therapeutic nanoparticle, the active ingredient comprising an ionizable group that is at least 70% ionizable in the aqueous phase, wherein the active ingredient comprises a histone deacetylase inhibitor selected from the group consisting of vorinostat (=suberoylanilide hydroxamic acid=SAHA), istodax, belinostat, apicidin, scriptaid, sodium butyrate, trichostatin A, entinostat, panobinostat, mocetinostat, romidepsin, tubastatin A, givinostat, dacinostat, quisinostat, pracinostat, droxinostat, abexinostat, ricolinostat, tacedinaline, tubacin, resminostat, citarinostat, santacruzamate, nexturastat A, tasquinimod, parthenolide, and any pharmaceutically acceptable salts thereof, and has a higher water solubility in pH 10 or above than in neutral pH.

2. The method of claim 1, wherein the active ingredient is a weak acid, and the pH of the aqueous phase is between 8 and 14.

3. The method of claim 1, wherein the active ingredient is a weak base, and the pH of the aqueous phase is between 1 and 7.

4. The method of claim 1, further comprising dissolving the active ingredient in a solvent selected from the group consisting of dimethyl sulfoxide (DMSO), acetonitrile, and acetone.

5. The method of claim 1, wherein the aqueous phase comprises a surfactant, a stabilizer, or both; and
the surfactant or the stabilizer is selected from the group consisting of sodium cholate, sodium dodecyl sulfate, poloxamer, Tweens, vitamin E, tocopheryl polyethylene glycol succinate (TPGS), ethylene glycol, glycerol, and polyvinyl alcohol (PVA).

6. The method of claim 1, wherein the organic solvent comprises a water-immiscible solvent selected from the group consisting of dichloromethane (DCM), chloroform, carbon tetrachloride, dichloroethane, diethyl ether, ethyl acetate, and toluene.

7. The method of claim 1, wherein the organic solvent comprises a water-miscible solvent selected from the group consisting of acetaldehyde, acetic acid, acetone, acetonitrile, cyclohexane, dimethylformamide, dioxane, ethanol, heptane, hexane, methanol, formic acid, ethylamine, dimethyl sulfoxide, pentane, propanol, pyridine, and tetrahydrofuran.

8. The method of claim 1, wherein the nanoparticle is prepared by emulsification; and the method further comprises:

a. forming a pre-emulsion organic phase comprising the amphiphilic polymer and the organic solvent;

b. combining the pre-emulsion organic phase with a pre-emulsion aqueous phase to form a pre-emulsion mixture; and c. emulsifying the pre-emulsion mixture to form an emulsion.

9. The method of claim 1, wherein the nanoparticle is prepared by nanoprecipitation, optionally in the presence of the active ingredient.

10. The method of claim 1, wherein the ionizable group is selected from the group consisting of hydroxamic acid group, carboxyl group, hydroxyl group, sulfhydryl group, phenolic group, amino group, imidazole group, guanidinium group, sulphonamide group, and imide group.

11. The method of claim 1, wherein the amphiphilic polymer comprises PLA-PEG having a weight averaged molecular weight of 2,000 to 60,000 daltons.

12. The method of claim 1, wherein the therapeutic nanoparticle comprises the active ingredient at a concentration of at least 4% (% w/w).

13. The method of claim 1, wherein the histone deacetylase inhibitor comprises quisinostat and any pharmaceutically acceptable salts thereof.

14. The method of claim 1, wherein a measured hydrodynamic diameter of the therapeutic nanoparticle is between 20-300 nm.

15. The method of claim 1, wherein a measured zeta potential of the therapeutic nanoparticle is between −35 and +10 mV.

16. The method of claim 1, wherein the therapeutic nanoparticle further comprises a second biologically active ingredient.

17. The method of claim 1, wherein the active ingredient and the nanoparticle electrostatically interact.

\* \* \* \* \*